us008937171B2

(12) United States Patent
Miyata et al.

(10) Patent No.: US 8,937,171 B2
(45) Date of Patent: Jan. 20, 2015

(54) NUCLEIC-ACID-RESPONSIVE GEL, METHOD FOR PRODUCING SAME, AND USE OF SAME

(75) Inventors: Takashi Miyata, Suita (JP); Tadashi Uragami, Suita (JP); Kaori Okawa, Gifu (JP)

(73) Assignees: Japan Science and Technology Agency, Saitama (JP); A School Corporation Kansai University, Osaka (JP)

( * ) Notice: Subject to any disclaimer, the term of this patent is extended or adjusted under 35 U.S.C. 154(b) by 547 days.

(21) Appl. No.: 12/448,857

(22) PCT Filed: Aug. 6, 2007

(86) PCT No.: PCT/JP2007/065384
§ 371 (c)(1),
(2), (4) Date: Oct. 30, 2009

(87) PCT Pub. No.: WO2008/084571
PCT Pub. Date: Jul. 17, 2008

(65) Prior Publication Data
US 2010/0081204 A1 Apr. 1, 2010

(30) Foreign Application Priority Data
Jan. 12, 2007 (JP) ................................ 2007-005227

(51) Int. Cl.
| C07H 21/04 | (2006.01) |
|---|---|
| B01D 57/02 | (2006.01) |
| C12Q 1/68 | (2006.01) |
| C12P 19/34 | (2006.01) |
| G01N 33/00 | (2006.01) |
| C07H 21/02 | (2006.01) |
| G01N 15/06 | (2006.01) |
| G01N 33/48 | (2006.01) |

(52) U.S. Cl.
CPC .................................... C12Q 1/6816 (2013.01)
USPC .......... 536/24.3; 204/450; 435/6.1; 435/6.11; 435/91.1; 436/94; 536/23.1; 536/24.33; 422/68.1

(58) Field of Classification Search
USPC ........... 435/6.1, 91.1, 183, 6.11; 436/94, 501; 536/23.1, 24.3, 24.33; 204/450; 422/50, 68.1
See application file for complete search history.

(56) References Cited

U.S. PATENT DOCUMENTS

| 5,739,946 | A | 4/1998 | Iwanaga et al. |
|---|---|---|---|
| 6,110,684 | A * | 8/2000 | Kemper et al. ............... 435/6.18 |
| 6,616,946 | B1 | 9/2003 | Meier et al. |
| 2002/0164589 | A1 * | 11/2002 | Taylor ............................. 435/6 |
| 2004/0146500 | A1 | 7/2004 | Miyata et al. |
| 2005/0209411 | A1 | 9/2005 | Nestler et al. |
| 2007/0156042 | A1 * | 7/2007 | Unal ............................. 600/410 |

FOREIGN PATENT DOCUMENTS

| CN | 1653094 | 8/2005 |
|---|---|---|
| EP | 1852454 | 11/2007 |
| EP | 1892519 | 2/2008 |
| JP | 09-302263 | 11/1997 |
| JP | 2002-239358 | 8/2002 |
| JP | 2005-106533 | 4/2005 |
| JP | 2006-137805 | 6/2006 |
| JP | 2006-138656 | 6/2006 |
| JP | 2006-161027 | 6/2006 |
| JP | 2006-257139 | 9/2006 |
| JP | 2007-046041 | 2/2007 |
| WO | WO 02/090990 | 11/2002 |

OTHER PUBLICATIONS

"Nucleotide & Nucleic Acid Properties". pp. 1 and 2. Printed on Dec. 23, 2011.*
1988 Stratagene catalog (p. 39). Published by Stratgene, 11011 North Torrey Pines Road, La Jolla, CA 92037, USA.*
Miyata et al., Preparation of bioconjugated hydrogels that response to target biomolecules. Polymer Preprints, pp. 1 and 2, Published on Sep. 11, 2006.*
Office Action dated Dec. 31, 2010 for corresponding Chinese Patent Application No. 200880014924 with English translation.
Miyata et al., "A reversibly antigen-responsive hydrogel", Nature, vol. 399, pp. 766-769 (1999).
Miyata et al., "Tumor marker-responsive behavior of gels prepared by biomolecular imprinting", PNAS, vol. 103, No. 5, pp. 1190-1193 (Jan. 31, 2006).
Hayashi et al., "pH-Sensitive Nanogel Possessing Reactive PEG Tethered Chains on the Surface", Macromolecules, vol. 37, pp. 5389-5396 (2004).
Nayak et al., "Soft Nanotechnology with Soft Nanoparticles", Angew. Chem. Int. Ed., vol. 44, pp. 7686-7708 (2005).

(Continued)

*Primary Examiner* — Frank Lu
(74) *Attorney, Agent, or Firm* — Harness, Dickey & Pierce, P.L.C.

(57) ABSTRACT

The present invention provides a nucleic-acid-responsive gel which allows (i) a larger volumetric change through structural design, (ii) adjustment of its recognition ability to recognize a nucleic acid, (iii) improvement of sensitivity, and (iv) flexible design according to, e.g., a sequence of target DNA. The nucleic-acid-responsive gel includes a probe formed of two single-stranded nucleic acids which are hybridized with each other. The probe is fixed within a network structure of a polymer gel. The two single-stranded nucleic acids are bound reversibly with each other.

12 Claims, 6 Drawing Sheets

(56) References Cited

OTHER PUBLICATIONS

Y. Murakami, et al., "Hybrid Hydrogels to Which Single-Stranded (ss) DNA . . . ", Macromolecules, vol. 38, No. 5, 2005, pp. 1535-1537.
Y. Murakami, et al., "DNA-Responsive Hydrogels That Can Shrink or Swell", Biomacromolecules, vol. 6 No. 6, 2005, pp. 2927-2929.
D. Umeno et al., "Affinity Adsorption Separation of Mutagenic Molecules . . . ", Anal. Chim. Acta. vol. 365, 1998, pp. 101-108.
T. Miyata et al., (2006) "Controlled Structures and Responsiveness of Stimuli-responsive Gels That Undergo Volume Changes in Responses to Biomolecules", Polymer Preprints, Japan, vol. 55, No. 2, pp. 4516-4517 1S14 The Society of Polymer Science, Japan, Published Sep. 5, 2006.
K. Ohkawa et al., (2006) "Synthesis of DNA-Responsive Gels Using Duplex DNAs as Crosslinking Points", Abstract of Lectures at $17^{th}$ Workshop on Polymer Gels, pp. 39-40, The Society of Polymer Science, Japan, Published Jan. 18, 2006.
K. Ohkawa, et al., (2006) "Synthesis of DNA-responsive Gels Having DNA Duplexes as Crosslinking Points and Their DNA-Recognition Behavior", Polymer Preprints, Japan, vol. 55, No. 1, p. 1957, The Society of Polymer Science, Japan, Published May 10, 2006.
T. Miyata, et al., (2006) "Synthesis of DNA-responsive Gels of Different Swelling and Shrinking Types and Their Response Behavior", Polymer Preprints, Japan, vol. 55, No. 2, pp. 5349-5350, The Society of Polymer Science, Japan, Published Sep. 5, 2006.
T. Miyata et al., (2007) "Structure Control and Response Behavior of Smart Gel Which Responds to Biomolecule", Papers at $11^{th}$ Kansai University Symposium on Innovative Science and Technology, Kansai University, pp. 157-158, Published Jan. 10, 2007.
T. Miyata et al., (2007) "Synthesis of Two DNA-responsive Gels That Swell or Shrink in Response to DNA Sequences", Abstract of Lectures at $18^{th}$ Research Workshop on Polymer Gels, pp. 27-28, The Society of Polymer Science, Japan, Published Jan. 9, 2007.
Office Action dated Nov. 1, 2012 issued in U.S. Appl. No. 12/598,904.
Office Action dated Jun. 11, 2012 issued in U.S. Appl. No. 12/598,904.
Miyata, T., et al. (2006) "Biomolecule-responsive behavior of smart gels having biomolecular complexes as reversible cross-links" 06AIChE Annual Meeting.
Office Action for Japanese Patent Application No. 2007-005227 dated Dec. 18, 2012 with English Translation.
Office Action dated Mar. 27, 2013 issued in U.S. Appl. No. 12,598,904.

* cited by examiner

NUCLEIC-ACID-RESPONSIVE GEL, METHOD FOR PRODUCING SAME, AND USE OF SAME

TECHNICAL FIELD

The present invention relates to a nucleic-acid-responsive gel, a method for producing the same, and use of the same. In particular, the present invention relates to a nucleic-acid-responsive gel capable of recognizing single nucleotide polymorphisms, a method for producing the same, and use of the same.

BACKGROUND ART

A stimuli-responsive gel that changes its structure in response to a change of an external environment, e.g., a change in pH or temperature, is highly expected as a next-generation soft material that has a sensing function, a processor function, and an effector function in combination. In particular, attempts have been recently started to synthesize a stimuli-responsive gel having such a molecular recognition ability that it swells or shrinks by recognizing a specific molecule related to a medical or environmental field. For example, the inventors of the present invention proposed molecular imprinting as a method for synthesizing a molecular-stimuli-responsive gel which responds to a biomolecule. The molecular imprinting proposed by the inventors of the present invention is such that a target molecule bound with a ligand monomer is incorporated into a gel, so that a binding state is memorized. By this method, the inventors succeeded in the synthesis of a gel which swells or shrinks in response to a biomolecule.

On the other hand, development of a genetic diagnosis technique and a genetic diagnosis material which allow effective and easy detection of a disease-related mutation of DNA is needed for realization of tailor-made medical care which allows prevention or treatment of a disease on the basis of personal genetic information. Although a stimuli-responsive gel is a highly-expected material as a genetic diagnosis material, only a few have been reported so far on DNA-responsive gels each of which recognizes and responds to a target DNA.

The reported DNA-responsive gels encompass a gel in which an end of a single-stranded nucleic acid which serves as a probe is fixedly bonded to a polymer compound having a network structure (see, e.g., Patent Literature 1 and Non-patent Literature 1). It was reported that the gel can detect whether hybridization between a nucleic acid to test and the single-stranded nucleic acid fixed to the gel occurs. The detection utilizes a fact that, in a case where the hybridization between the nucleic acid to test and the single-stranded nucleic acid occurs, the gel shrinks for the reason that water molecules therein are discharged outside the gel due to dehydration consequently caused by the hybridization.

In addition, a stimuli-responsive gel to which single-stranded DNA is introduced so as to cross-link the gel (i.e., introduced as a cross-linking point) is reported as a stimuli-responsive gel which does not only shrink, but also does shrink or swell in response to DNA (see, e.g., Non-patent Document 2). According to the report, the stimuli-responsive gel swells in response to a single-stranded DNA complementary to the introduced single-stranded DNA in a case where the introduced single-stranded DNA has a stem-loop. On the other hand, the stimuli-responsive gel shrinks in response to a single-stranded DNA complementary to the introduced single-stranded DNA in a case where the introduced single-stranded DNA has no intramolecular base pair. In addition, according to the report, the reason why the gel swells or shrinks is that the single-stranded DNA introduced in the gel and the single-stranded DNA complementary therewith are bound into a double-stranded DNA, thereby changing the shape of the single-stranded DNA introduced in the gel.

Furthermore, a gel is disclosed in which a vinylated double-stranded DNA is fixed in a network structure (see, e.g., Non-patent Document 3). According to the report, DNA-binding vinylated psoralen which causes two base strands of DNA to irreversibly bind with each other is introduced to the whole DNA (i.e., to regions which are not particularly limited, except terminals of the DNA), and "wholly-vinylated" DNA thus obtained is fixed in the gel. It is also reported that a DNA-fixed gel thus obtained makes it possible to trap various DNA-binding substances. In the case of the DNA-fixed gel thus obtained, however, it is considered that the DNA fixed in the gel completely loses its base recognition ability because the two base strands of the DNA introduced in the gel are irreversely bound with each other. Therefore, the DNA-fixed gel does not have responsivity to a nucleic acid.

CITATION LIST

Patent Literature 1
Japanese Patent Application Publication, Tokukai, No. 2005-106533 A (Publication Date: Apr. 21, 2005)
Non-Patent Literature
Y. Murakami, M. Maeda, Macromolecules, 38, 1535-1537 (2005)
Non-Patent Literature 2
Y. Murakami, M. Maeda, Biomacromolecules, 6, 2927-2929 (2005)
Non-Patent Literature 3
Umeno et al., Analytica Chimica Acta, 365, 101-108 (1998)

SUMMARY OF INVENTION

Technical Problem

Patent Literature 1 (or Non-patent Literature 1) and Non-patent Literature 2 each describe that a degree of swelling of a DNA-responsive gel disclosed therein varies even by one base mismatch of DNA. However, such conventional DNA-responsive gels are unsatisfactory in that they do not allow adjustment of their recognition abilities and they are insufficient in sensitivity and in amount of a volumetric change. Therefore, there is a call for a DNA-responsive gel and a nucleic-acid-responsive gel which excel in these capabilities.

The present invention was made in view of the problem. An object of the present invention is to realize a nucleic-acid-responsive gel that is (i) adjustable in its recognition ability to recognize a nucleic acid, (ii) improved in sensitivity, (iii) capable of showing a greater volumetric change, and (iv) more flexibly designable according to, e.g., a base sequence of target DNA.

Solution to Problem

In order to attain the object of the present invention, the inventors of the present invention synthesized, as a result of diligent study, a totally novel nucleic-acid-responsive gel in which a probe formed of two single-stranded nucleic acids hybridized with each other is fixed in a network structure of a polymer gel as gel cross-linking points. The inventors found that, when a target nucleic acid which is completely complementary to any one of the two single-stranded nucleic acids which formed the probe is present, the nucleic-acid-responsive gel recognizes the target nucleic acid and swells. The inventors also found that the nucleic-acid-responsive gel utilizing the two single-stranded nucleic acids hybridized with each other as its probe is adjustable in binding force between the two single-stranded nucleic acids by changing the number of base mismatches, a temperature, and/or the like, in a case where the probe contains one or more base pair mismatches in a hybridized part between the two single-stranded nucleic acids. The inventors further found that the nucleic-acid-responsive gel shows different swelling behaviors in response to (i) a nucleic acid which was completely complementary to any one of the two single-stranded nucleic acids and to (ii) a nucleic acid which had one base mismatch in relation to any one of the two single-stranded nucleic acids, respectively, whereby the nucleic-acid-responsive gel is capable of recognizing a difference between two nucleic acids even if only one base is different. The present invention was achieved based on the findings.

In order to attain the object, a nucleic-acid-responsive gel of the present invention includes: a probe formed of two single-stranded nucleic acids which are hybridized with each other, the probe being fixed inside a network structure of a polymer gel, the probe being formed of the two single-stranded nucleic acids which are reversibly bound with each other.

According to the arrangement, the probe is formed of a double strand. This makes it possible to utilize a competitive effect more, as compared to the case of a single strand. This makes it possible to obtain a high sensitivity. In a case where, e.g., the probe has one or more base mismatches in a part where the two single-stranded nucleic acids are hybridized, it is possible to adjust a binding force between the two single-stranded nucleic acids by changing the number of base mismatches and/or a temperature. That is, this makes it possible to adjust a recognition ability to recognize a nucleic acid.

The nucleic-acid-responsive gel is arranged such that the probe is fixed inside the network structure of the polymer gel so as to form a cross-linkage in such a manner that each of the two single-stranded nucleic acids binds with a polymer compound constituting the network structure of the polymer gel.

According to the arrangement, the probe is fixed with the inside of the network structure of the polymer gel so as to form a cross-linkage. In a case where the two single-stranded nucleic acids hybridized with each other are dissociated (melted) from each other, the cross-linkage is disconnected, and thereby cross-linking points decrease. This produces an effect in that the nucleic-acid-responsive gel swells. Accordingly, the arrangement in which a double strand is used as a probe produces a synergetic effect of an osmotic change and a decrease of cross-linking points while an arrangement in which a single strand is used as a probe causes a volumetric change only by an osmotic change.

The nucleic-acid-responsive gel of the present invention is preferably arranged such that, in a part where the two single-stranded nucleic acids are hybridized with each other, the probe has one or more base mismatches.

According to the arrangement, the probe has one or more base mismatches in a part where the two single-stranded nucleic acids are hybridized with each other. Accordingly, a bond between the two single-stranded nucleic acids in the part is unstable, as compared to a case where the two single-stranded nucleic acids which form the probe are completely complementary to each other. Therefore, in the presence of (i) a nucleic acid which is completely complementary to (ii) any one of the two single-stranded nucleic acids which form the probe, the arrangement above produces an effect of causing a strand exchange between the other one of the two single-stranded nucleic acids and (i), so that a more stable double strand is formed.

The nucleic-acid-responsive gel of the present invention is preferably arranged such that: each of the two single-stranded nucleic acids has a 5' terminal bound with the polymer compound constituting the network structure of the polymer gel. The nucleic-acid-responsive gel of the present invention may be arranged such that: each of the two single-stranded nucleic acids has a 3' terminal bound with the polymer compound constituting the network structure of the polymer gel.

It is easy to introduce to a 5' terminal or a 3' terminal a group which allows a single-stranded nucleic acid to bind with the polymer compound. This makes it possible to easily bind the probe with the network structure of the polymer gel.

The nucleic-acid-responsive gel of the present invention is arranged such that: each of the two single-stranded nucleic acids is DNA, RNA, or PNA.

The nucleic-acid-responsive gel of the present invention is preferably arranged such that: the polymer gel is: a polymer gel obtained by polymerizing a monomer including at least one monomer selected from the group consisting of (meth)acrylamide, (meth)acrylic acid, 2-hydroxyethyl (meth)acrylate, alkyl (meth)acrylate, N,N'-dimethyl (meth)acrylamide, N-isopropyl (meth)acrylamide, vinyl acetate, and allylamine; or a polymer gel obtained in such a manner that at least one polymer compound selected from the group consisting of poly(meth)acrylamide, poly(meth)acrylic acid, poly-2-hydroxyethyl methacrylate, polyalkyl (meth)acrylate, poly-N,N'-dimethyl (meth)acrylamide, poly-N-isopropyl (meth)acrylamide, polyvinyl alcohol, polyallylamine, cellulose, chitosan, alginic acid, and derivatives thereof is reacted with a cross-linking agent so that the polymer compound has the network structure.

The use of the monomer or the polymer compound makes it possible to obtain a polymer gel which swells by absorbing water.

The nucleic-acid-responsive gel of the present invention is preferably arranged such that: the number of bases of the two single-stranded nucleic acids which form the probe is 2 or more, but 10000 or less.

The number of bases of each strand in the range above makes it possible to form a sufficiently stable double strand. In addition, for the reason that the number is 10000 or less, the arrangement also makes it possible to sufficiently diffuse target DNA in the gel.

The nucleic-acid-responsive gel of the present invention is a nucleic-acid-responsive gel which swells in response to a nucleic acid.

By swelling in response to a nucleic acid, the nucleic-acid-responsive gel of the present invention can convert a subtle difference between base sequences of nucleic acids into macro information such as a volumetric change. This makes it possible to provide a technique which is easier to handle.

The nucleic-acid-responsive gel of the present invention is a nucleic-acid-responsive gel which decreases in cross-link density in response to a/the nucleic acid.

By decreasing in cross-link density in response to a nucleic acid, the nucleic-acid-responsive gel of the present invention makes it possible to recognize a DNA sequence etc. and to convert it to easy-to-handle information, i.e., a volume of the gel.

In order to attain the object of the present invention, the nucleic-acid-responsive gel of the present invention may be a nucleic-acid-responsive gel obtained by copolymerizing a probe with a monomer in presence or absence of a cross-linking agent, the probe being formed of two single-stranded nucleic acids hybridized with each other each having a reactive functional group, and the monomer including at least one monomer selected from the group consisting of (meth)acrylamide, (meth)acrylic acid, 2-hydroxyethyl (meth)acrylate, alkyl-(meth)acrylate, N,N'-dimethyl (meth)acrylamide, N-isopropyl (meth)acrylamide, vinyl acetate, and allylamine.

In order to attain the object of the present invention, the nucleic-acid-responsive gel of the present invention may be a nucleic-acid-responsive gel obtained by a process comprising: (a) binding a probe formed of two single-stranded nucleic acids hybridized with each other each having a reactive functional group, with a polymer compound; and (b) reacting a resultant obtained in the step (a) with a cross-linking agent, so that the resultant has a network structure, the polymer compound being at least one selected from the group consisting of poly(meth)acrylamide, poly(meth)acrylic acid, poly-2-hydroxyethyl methacrylate, polyalkyl (meth)acrylate, poly-N, N'-dimethyl (meth)acrylamide, poly-N-isopropyl (meth) acrylamide, polyvinyl alcohol, polyallylamine, cellulose, chitosan, alginic acid, and derivatives thereof.

In order to attain the object of the present invention, a method for producing the nucleic-acid-responsive gel of the present invention is a method for producing a nucleic-acid-responsive gel, including: (a) introducing a reactive functional group to each of two single-stranded nucleic acids to be hybridized with each other; (b) forming a double strand as a probe by hybridizing the two single-stranded nucleic acids having the respective reactive functional group introduced in the step (a); and (c) copolymerizing, in presence or absence of a cross-linking agent, the probe obtained in the step (b) with a monomer which forms a polymer gel.

In order to attain the object, a method for producing the nucleic-acid-responsive gel of the present invention may be a method for producing a nucleic-acid-responsive gel, including: (a) introducing a reactive functional group in two single-stranded nucleic acids to be hybridized with each other; (b) forming a double strand as a probe by hybridizing the two single-stranded nucleic acids having the reactive functional group introduced in the step (a); (c) binding the probe obtained in the step (b) with a polymer compound; and, (d) cross-linking, by reaction with a cross-linking agent, the polymer compound obtained in the step (c), so that the polymer compound has a network structure.

According to the arrangement, the probe is formed of a double strand. This makes it possible to utilize a competitive effect more, in contrast to the case of a single strand. As a result, it is possible to obtain a high sensitivity. In a case where, e.g., the probe has one or more base mismatches in a part where the two single-stranded nucleic acids are hybridized, it is possible to adjust a binding force between the two single-stranded nucleic acids by changing the number of base mismatches and/or a temperature. This makes it possible to adjust a recognition ability to recognize a nucleic acid.

A method of the present invention for detecting a target nucleic acid, includes: contacting a nucleic-acid-responsive gel of the present invention with a specimen containing a nucleic acid; and detecting, from a volumetric change of the nucleic-acid-responsive gel, whether or not a strand exchange due to the target nucleic acid occurs.

In order to attain the object, a method of the present invention for controlling detection accuracy of a method for detecting a target nucleic acid, the method for detecting a target nucleic acid, including: (a) contacting a nucleic-acid-responsive gel of the present invention with a specimen containing a nucleic acid; and (b) detecting, from a volumetric change of the nucleic-acid-responsive gel, whether or not a strand exchange due to the target nucleic acid occurs, the method for controlling detection accuracy of the method for detecting the target nucleic acid, comprising: adjusting a temperature for performing the step (a).

Stability of a hydrogen bond between two single-stranded nucleic acids which form a probe and stability of a hydrogen bond between a target nucleic acid and any one of the two single-stranded nucleic acids which is intended to hybridize with the target nucleic acid are closely related to a temperature at which the detection is performed. Therefore, by utilizing the balance of the stability, the method of the present invention for detecting a target nucleic acid makes it possible to control detection accuracy such as detection sensitivity, selectivity of a base sequence of a nucleic acid to be detected, etc.

A nucleic acid detection kit and a nucleic acid detection apparatus of the present invention include the nucleic-acid-responsive gel of the present invention.

Advantageous Effects of Invention

As described above, the nucleic-acid-responsive gel of the present invention includes a probe formed of two single-stranded nucleic acids which are hybridized with each other which probe is fixed inside a network structure of a polymer gel. The two single-stranded nucleic acids are reversibly bound with each other. Accordingly, since the probe is formed of a double strand, it is possible to utilize a competitive effect more, in contrast to the case of a single strand. As a result, it is possible to obtain a high sensitivity. In a case where, e.g., the probe has one or more base mismatches in a part where the two single-stranded nucleic acids are hybridized, it is possible to adjust a binding force between the two single-stranded nucleic acids by changing the number of base mismatches and/or a temperature. This makes it possible to adjust a recognition ability to recognize a nucleic acid.

BRIEF DESCRIPTION OF DRAWINGS

FIG. 7(a) illustrates a case where the nucleic-acid-responsive gel is brought into contact with a target nucleic acid under low temperature. FIG. 7(b) illustrates a case where the temperature is adjusted so that the nucleic-acid-responsive gel has the highest responsiveness. FIG. 7(c) illustrates a case where the temperature is high.

DESCRIPTION OF EMBODIMENTS

Figure 1:
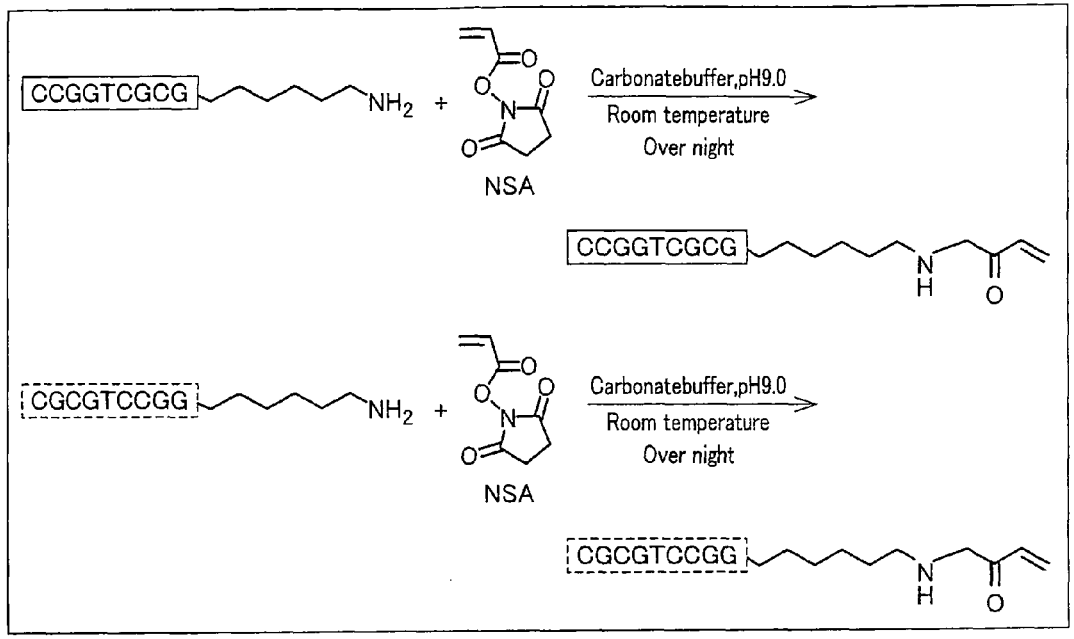
FIG. 1 is a view showing reaction formulas for synthesizing vinyl-group-introduced oligo DNA in Examples.

The following describes the present invention in the order of (I) a nucleic-acid-responsive gel of the present invention, (II) a method for producing the same, and (III) use of the same.

(I) Nucleic-Acid-Responsive Gel of Present Invention

A nucleic-acid-responsive gel of the present invention includes a probe formed of two single-stranded nucleic acids which are hybridized with each other which probe is fixed inside a network structure of a polymer gel. The two single-stranded nucleic acids are reversibly bound with each other.

The "polymer gel" is not particularly limited, provided that it is a gel obtained by causing a polymer compound having a network structure to swell due to liquid absorption. For example, the polymer gel may be a hydrogel obtained by causing a polymer compound having a network structure to swell due to water absorption, or an organogel obtained by causing a polymer compound having a network structure to swell due to absorption of an organic solvent. Among these, the polymer gel is more preferably a hydrogel from a viewpoint of stability of a nucleic acid. The nucleic-acid-responsive gel of the present invention shows response to a nucleic acid when the nucleic-acid-responsive gel is in a swollen state. Note that, in the present invention, the "polymer gel" and the nucleic-acid-responsive gel also encompass a gel dried by removing water, an organic solvent, or the like, from a swollen gel.

In the nucleic-acid-responsive gel of the present invention, a probe fixed with the inside of the network structure of the polymer gel is formed of two single-stranded nucleic acids hybridized with each other. It is sufficient that the two single-stranded nucleic acids are at least partly hybridized. In other words, the two single-stranded nucleic acids may be hybridized wholly, or may be hybridized partly so as to have a part which is not hybridized.

"Hybridize" means that bases of two homologous single-stranded nucleic acids are bound with each other by hydrogen bond so as to form a relatively stable double strand. In general, hybridization can occur in a case where two single-stranded nucleic acids are completely complementary or almost complementary to each other. In the present invention, two single-stranded nucleic acids may be completely complementary to each other in a part where they are hybridized with each other, or, alternatively, may have one or more base mismatches in the part. In other words, the probe may have no base mismatch in the part, or, may have one or more base mismatches. "Base mismatch" means a combination of bases by which a normal base pair such as a pair of guanine (G) and cytosine (C) or a pair of adenine (A) and thymine (T) cannot be formed.

The probe is formed of two single-stranded nucleic acids which are reversibly bound with each other. In other words, reaction can progress in a direction in which the two single-stranded nucleic acids are dissociated from each other, due to a change of a condition such as a temperature and/or due to the presence of another nucleic acid, although respective base moieties of the two single-stranded nucleic acids are bound by hydrogen bond. In this respect, the reaction is reversible.

Figure 5:
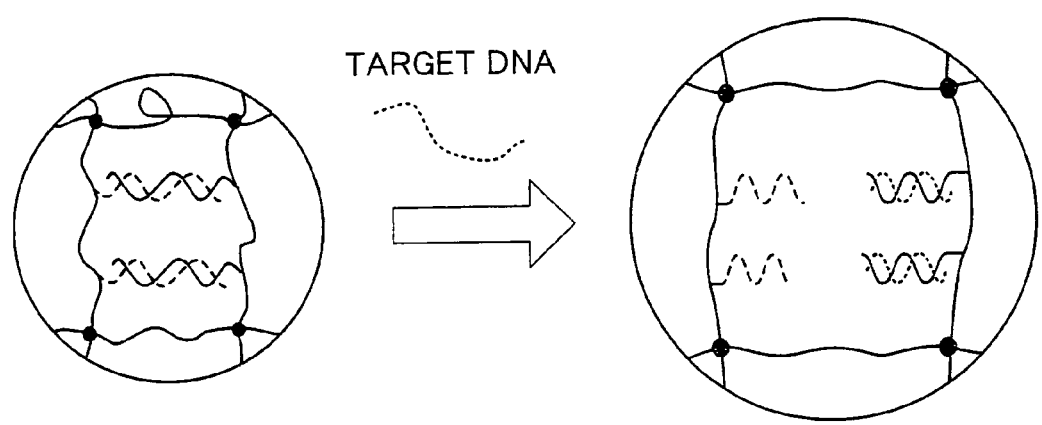
FIG. 5 is a view schematically illustrating how the nucleic-acid-responsive gel recognizes target DNA and swells.

In the nucleic-acid-responsive gel of the present invention, the probe is fixed inside the network structure of the polymer gel. Specifically, the probe is fixed inside the network structure of the polymer gel so as to form a cross-linkage in such a manner that each of the two single-stranded nucleic acids which form the probe binds with the polymer compound constituting the network structure of the polymer gel. That is, the probe is bound with the polymer compound so as to form a cross-linkage within the network structure of the gel, as is schematically illustrated in the left circle in FIG. 5. In FIG. 5, the black circles represent cross-linking points. A cross-linkage is formed in such a manner that two single-stranded nucleic acids represented in FIG. 5 by a continuous line and a dashed line, respectively, bind with the network structure of the gel. That is, the cross-linkage is completed by the hybridization of the two single-stranded nucleic acids, each of which binds, at one end, with the polymer compound constituting the network structure of the gel. It is considered that, with the arrangement, dissociation (melting) of the double-stranded nucleic acids (two single-stranded nucleic acids hybridized with each other) causes a disconnection of a cross-linkage as is schematically illustrated in the right circle in FIG. 5, and cross-linking points are reduced accordingly. As a result, the nucleic-acid-responsive gel swells, as is generally known that the lower the cross-link density, the higher the swelling ratio of a polymer gel.

As described above, the nucleic-acid-responsive gel of the present invention utilizes a mechanism by which dissociation of the double-stranded nucleic acids (two single-stranded nucleic acids hybridized with each other) serving as cross-linking points causes reduction of a cross-linkage thereby to swell the nucleic-acid-responsive gel. Therefore, the nucleic-acid-responsive gel has potential to greatly change its volume, provided that a structural design of the nucleic-acid-responsive gel permits the change. A conventional nucleic-acid-responsive gel to which a single-stranded nucleic acid is introduced changes its volume only due to a change in osmotic pressure applied thereon. In the case of the nucleic-acid-responsive gel of the present invention, in contrast, it is possible to expect a synergetic effect brought by both a change in osmotic pressure and a change in cross-link density.

In the nucleic-acid-responsive gel of the present invention, as described above, the probe is formed of two single-stranded nucleic acids which are hybridized with each other via reversible bonding. Therefore, in the presence of another nucleic acid which forms a more stable double strand in combination with any one of the two single-stranded nucleic acids which form the probe, or which competitively hybridizes with any one of the two single-stranded nucleic acids, the another nucleic acid replaces the other one of the two single-stranded nucleic acids hybridized with each other. A strand exchange thus occurs.

In a case where the probe has one or more base mismatches in its hybridized part, the bonding between the two strands in the hybridized part becomes unstable, as compared to a case where the two strands are completely complementary to each other. Therefore, in the presence of another nucleic acid capable of forming a more stable double strand, such as the one completely complementary to any one of the two single-stranded nucleic acids which form the probe, a strand exchange occurs to hybridize the one of the two single-stranded nucleic acids with the another nucleic acid in exchange of the other one of the two single-stranded nucleic acids, so that a more stable double strand is formed as is illustrated in the right circle in FIG. 5. As a result, a cross-linkage is disconnected, thereby reducing cross-linking points. It is considered that the nucleic-acid-responsive gel swells accordingly. That is, the two single-stranded nucleic acids which form the probe bind with the inside of the network structure of the gel, and the cross-linking points formed in positions where the two single-stranded nucleic acids bind with the network structure of the gel are reversible cross-linking points. Although FIG. 5 illustrates target DNA as a nucleic acid which is completely complementary to any one of the two single-stranded nucleic acids, DNA is replaced with nucleic acid here.

As described above, the aforementioned strand exchange between nucleic acids occurs in the presence of another nucleic acid capable of forming a more stable double strand. However, the strand exchange is not limited to this, but also occurs, e.g., in the presence of another nucleic acid capable of forming an equally stable double strand in combination with any one of two single-stranded nucleic acids hybridized with each other in such a manner that another nucleic acid competitively reacts with the one of the two single-stranded nucleic acids hybridized with each other.

In a case where the hybridized part has one or more base mismatches, the number of base mismatches is not particularly limited, provided that an upper limit of the number is in a range in which hybridization of two single-stranded nucleic acids is not hindered. An upper limit of the number of base mismatches varies depending on a length of each single-stranded nucleic acid to be introduced, a type of a solvent to be used to swell the nucleic-acid-responsive gel, a solvent content of the nucleic-acid-responsive gel, a concentration and type of a salt in the nucleic-acid-responsive gel, a temperature in the nucleic-acid-responsive gel, a base composition such as a ratio between GC and AT in the nucleic-acid-responsive gel, a pH in the nucleic-acid-responsive gel, etc. For example, the number of base mismatches is 1, 2, 3, 4, or 5. In the case of, e.g., two base mismatches, a binding force between two single-stranded nucleic acids becomes weaker as compared to the case of one base mismatch. By changing the number of base mismatches as described above, it is possible to change a binding force between two single-stranded nucleic acids. This makes it possible to freely adjust the recognition ability of a nucleic-acid-responsive gel to be obtained. Further, it is possible to change a binding force between two single-stranded nucleic acids, by changing a temperature. This makes it possible to further improve the recognition ability.

The nucleic-acid-responsive gel of the present invention is not particularly limited in types of the bonding between the two single-stranded nucleic acids which form the probe and the polymer compound constituting the network structure. Preferably, the bonding is chemical bond such as covalent bond, ionic bond, or coordinate bond. This makes it possible to stably fix the probe inside the network structure of the polymer gel.

The nucleic-acid-responsive gel of the present invention is not particularly limited in positions where the two single-stranded nucleic acids binds with the polymer compound, provided that the probe is fixed inside the network structure of the polymer gel so as to form cross-linkage in such a manner that the two single-stranded nucleic acids which form the probe binds respectively with the polymer compound constituting the network structure. For example, respective 5' terminals of the two single-stranded nucleic acids may be bound with the polymer compound constituting the network structure of the polymer gel. Alternatively, respective 3' terminals of the two single-stranded nucleic acids may be bound with the polymer compound constituting the network structure of the polymer gel. The 5' terminal and the 3' terminal each allow easy introduction thereto of a group for binding the single-stranded nucleic acid with the polymer compound. This makes it possible to easily bind the probe with the network structure of the polymer gel.

The single-stranded nucleic acids which form the probe may be DNA, RNA, or PNA. The two single-stranded nucleic acids may be two single strands of DNA, two single strands of RNA, or two single strands of PNA. Alternatively, the two single-stranded nucleic acids can be a combination of different two types of nucleic acids selected from the group consisting of DNA, RNA, and PNA.

The two single-stranded nucleic acids which form the probe are not particularly limited in length, and may have any length. However, for example, the single-stranded nucleic acids are preferably 2 or more but 10000 or less, or more preferably, 5 or more but 500 or less in number of bases. A single-stranded nucleic acid with a length of 2 or more bases is preferable because it can be bound with its counterpart with a proper binding force when the single-stranded nucleic acid is hybridized. Further, a single-stranded nucleic acid with a length of 10000 or less bases is preferable, because the single-stranded nucleic acid of such a size allows easy diffusion of target DNA within the network structure of the gel.

The polymer compound which can be used as the polymer gel is not particularly limited, provided that the polymer compound has the network structure and swells by absorbing water or an organic solvent. More preferably, the polymer gel is the one which swells by absorbing water. It is also more preferable that the polymer gel is obtained by polymerizing and cross-linking a hydrophilic monomer. For example, the monomer may be one of the following or a combination of two or more of the following: (meth)acrylic acid; alkyl (meth) acrylate; maleic acid; vinylsulfonic acid; vinylbenzene-sulfonic acid; (meth)acrylamide; acrylamidealkylsulfonic acid; (meth)acrylonitrile; an amino-substituted (meth)acrylamide such as dimethylaminopropyl (meth)acrylamide; an amino-substituted alkyl (meth)acrylate such as dimethylaminoethyl (meth)acrylate, diethylaminoethyl (meth)acrylate, or dimethylaminopropyl (meth)acrylate; a hydroxyethyl-methacrylate such as 2-hydroxyethyl (meth)acrylate; styrene; vinylpyridine; vinylcarbazole; dimethylaminostyrene; an alkyl-substituted (meth)acrylamide such as N-isopropyl (meth)acrylamide or N,N'-dimethyl (meth)acrylamide; vinyl acetate; allylamine; and the like. Among them, more preferable monomers are (meth)acrylamide; (meth)acrylic acid; alkyl (meth)acrylate; a hydroxyethylmethacrylate such as 2-hydroxyethyl (meth)acrylate; N,N'-dimethyl (meth)acrylamide; N-isopropyl (meth)acrylamide; vinyl acetate; allylamine; and the like. Further another monomer may be used in combination with any one(s) of these monomers, provided that an ability of a nucleic-acid-responsive gel to be obtained is not adversely affected. In the present Description, "(meth) acryl" encompasses both "acryl" and "methacryl."

The polymer compound is preferably the one cross-linked through copolymerization or reaction with a cross-linking agent containing two or more reactive functional groups in one molecule. The cross-linking agent may be a conventional cross-linking agent where appropriate. Preferable examples of the cross-linking agent are: cross-linkable monomers having a polymerizable functional group such as ethyleneglycol di(meth)acrylate, propyleneglycol di(meth)acrylate, N,N'-methylene-bis(meth)acrylamide, tolylenediisocyanate, divinylbenzene, or polyethyleneglycol di(meth)acrylate; glutaraldehyde; polyhydric alcohol; polyamine; polycarboxilic acid; and metal ions. The cross-linking agents can be used singly, or, in combination of two or more. The polymer compound may be the one cross-linked only by the probe of the present invention. In this case, the polymer compound is copolymerized with the probe, with no use of the cross-linking agent.

Examples of the polymer compound which can be used as the polymer gel are: poly(meth)acrylamide; poly-N-isopropyl(meth)acrylamide; poly-N,N'-dimethyl(meth)acrylamide; poly-2-hydroxyethylmethacrylate; (i) poly(meth)acrylic acid, poly-alkyl(meth)acrylate, polymaleic acid, polyvinylsulfonic acid, polyvinylbenzenesulfonic acid, polyacrylamidealkylsulfonic acid, polydimethylaminopropyl (meth)acrylamide, polyvinyl alcohol, polyethylene glycol, or polypropylen glycol and (ii) copolymers of (i) and (meth)acrylamide, hydroxyethyl(meth)acrylate, alkyl (meth)acrylate, or the like; complexes of polydimethylaminopropyl (meth)acrylamide and polyvinyl alcohol; complexes of polyvinyl alcohol and poly(meth)acrylic acid; calboxyalkyl cellulose metal salt; poly(meth)acrylonitirile; alginic acid; chitosan; polyallylamine; cellulose; derivatives thereof; cross-linked products thereof; and metal salts thereof. Preferable polymer compounds are, among them, poly(meth)acrylamide, poly(meth)acrylic acid, poly-2-hydroxyethylmethacrylate, poly-alkyl(meth)acrylate, poly-N,N'-dimethyl (meth)acrylamide, poly-N-isopropyl(meth)acrylamide, polyvinyl alcohol, polyallylamine, cellulose, chitosan, alginic acid, and derivatives thereof. A molecular weight of the polymer compound is preferably not less than 1000 but not more than 1000000. A molecular weight in the range preferably allows easy synthesis of a polymer gel by use of a moderate amount of the cross-linking agent.

The nucleic-acid-responsive gel of the present invention is used in its swollen state, for detecting a nucleic acid. The nucleic-acid-responsive gel of the present invention swells by further absorbing a liquid in response to a nucleic acid, thereby changing its volume. The liquid above is not particularly limited, but may be water, a water-based buffer solution, or an organic solvent. Examples of the liquid are: water; water-based buffer solutions such as a phosphate buffer solution, a Tris buffer solution, and an acetate buffer solution; alcohols such as methanol, ethanol, 1-propanol, 2-propanol, 1-butanol, 2-butanol, isobutyl alcohol, and isopentyl alcohol; ketones such as acetone, 2-butanone, 3-pentanone, methylisopropyl ketone, methyl n-propyl ketone, 3-hexanon, and methyl n-butyl ketone; ethers such as diethyl ether, diisopropyl ether, tetrahydrofuran, and tetrahydropyran; esters such as ethyl acetate; amides such as dimethylformamide and dimethylacetamide; dimethylsulfoxide; nitriles such as acetonitrile; propylene carbonate; lower saturated hydrocarbons such as pentane, hexane, and cyclohexane; xylene; toluene; and a mixture of two or more thereof. Among them, more preferably, the liquid is water or a water-based buffer solution, from a viewpoint of stability of a nucleic acid. A ratio of the liquid contained in the nucleic-acid-responsive gel of the present invention when the nucleic-acid-responsive gel swells to reach equilibrium is preferably 30 wt % or more but 99.9 wt % or less, and more preferably, 70 wt % or more but 99 wt % or less, based on a total weight of the nucleic-acid-responsive gel and the liquid in the nucleic-acid-responsive gel, although the ratio varies depending on a cross-link density of the polymer gel, a type of the polymer, a type of the solvent, a temperature, a pH, an ion intensity, etc. These ranges are preferable because when the ratio is within the ranges, the nucleic-acid-responsive gel can have an adequate strength and a polymer network structure which allows a target nucleic acid to diffuse in the gel.

A cross-link density of the nucleic-acid-responsive gel of the present invention is preferably not less than 0.1 (mol/m$^3$) but not more than 500 (mol/m$^3$), or, more preferably, not less than 1 (mol/m$^3$) but not more than 100 (mol/m$^3$). A cross-link density in any of the ranges preferably allows the nucleic-acid-responsive gel to greatly change its volume, and further, to have an adequate strength. In the present Description, "cross-link density" refers to a value obtained by a method shown in Examples described later.

A probe content of the nucleic-acid-responsive gel of the present invention is not particularly limited, provided that the content is in a range in which the nucleic-acid-responsive gel can swell in response to a nucleic acid. The probe content is preferably 0.01 wt % or more, more preferably, 0.1 wt % or more, or further more preferably, 1 wt % or more, where the weight of the nucleic-acid-responsive gel in a dried state is put as 100 wt %. The higher the probe content, the larger the change in cross-link density caused in response to a nucleic acid. This makes it possible to improve the recognition ability to recognize a target nucleic acid. The more probes provided in the gel, the higher the recognition ability. Accordingly, there is no upper limit of the probe content. Since nucleic acids are expensive, the probe content is preferably 50 wt % or less where the weight of the nucleic-acid-responsive gel in the dried state is put as 100 wt %.

Figure 6:
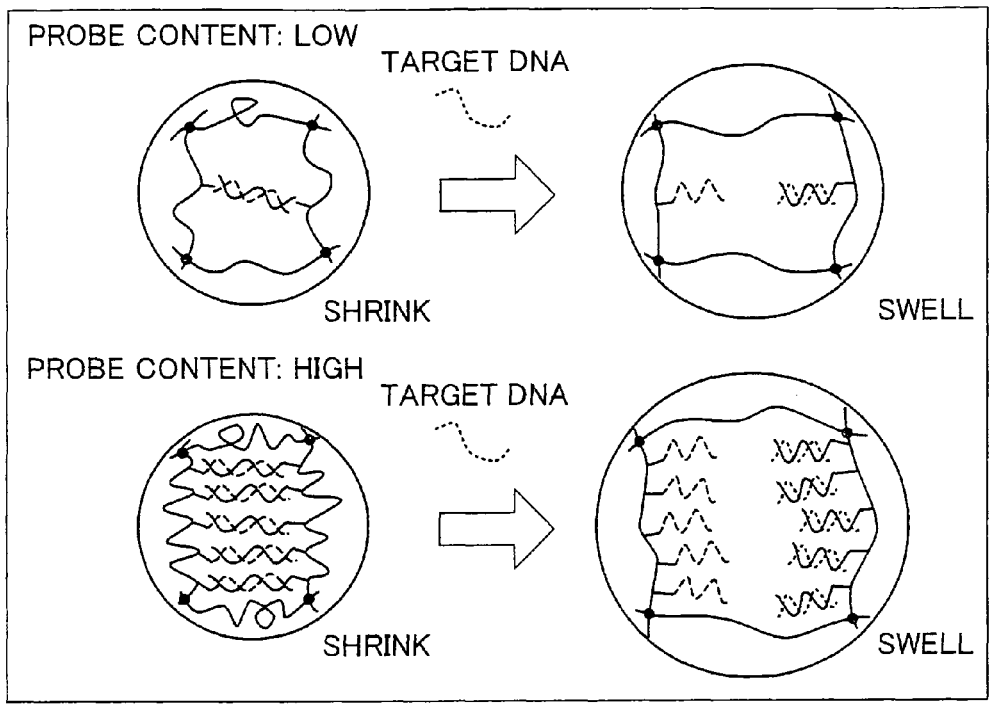
FIG. 6 is a view schematically illustrating how a degree of a change in cross-link density caused by adding target DNA to the nucleic-acid-responsive gel was varied depending on a probe content of the nucleic-acid-responsive gel.

With reference to FIG. 6, the following explains the reason why the higher the probe content, the larger the change in cross-link density caused in response to a nucleic acid. FIG. 6 is a view schematically illustrating how a degree of a change in cross-link density caused by adding target DNA to the nucleic-acid-responsive gel varies depending on the probe content of the nucleic-acid-responsive gel.

As illustrated in FIG. 6, more cross-linked structures are formed in a nucleic-acid-responsive gel having a higher probe content, as compared to the case of a lower probe content.

Accordingly, in the nucleic-acid-responsive gel having a higher probe content, more cross-linked structures are disconnected upon provision of target DNA. Therefore, the nucleic-acid-responsive gel having a higher probe content undergoes a larger change in cross-link density caused by addition target DNA to the gel, as compared to the case of a lower probe content.

The nucleic-acid-responsive gel of the present invention is not particularly limited in its shape, but may be in any shape. That is, a preferable shape can be suitably chosen in accordance with a use. Examples of a shape of the nucleic-acid-responsive gel are: a cylindrical shape, a plate-like shape, a film-like shape, a particulate shape, a spherical shape, and a shape of a rectangular parallelepiped. If the nucleic-acid-responsive gel is used in, e.g., a sensor chip, the nucleic-acid-responsive gel preferably has a shape like a thin film, a film-like shape, or the like. If the nucleic-acid-responsive gel is used in a diagnostic reagent, the nucleic-acid-responsive gel preferably has a particulate shape or the like.

In order to give a desired shape to the nucleic-acid-responsive gel of the present invention, it is possible to employ, e.g., a method in which a monomer composition or the like which is a raw material of the nucleic-acid-responsive gel is poured into a desired mold, and then, polymerization is performed within the mold.

A size of the nucleic-acid-responsive gel is not also particularly limited. That is, a preferable size can be suitably chosen depending on use. For example, it is preferable to choose a small size for use in a sensor etc. In a case where the nucleic-acid-responsive gel for use in a sensor etc. has a spherical shape, a diameter thereof is preferably not less than 0.01 μm but not more than 100 μm. The smaller the size of the nucleic-acid-responsive gel, the faster the response speed. Therefore, the nucleic-acid-responsive gel having a smaller size can be suitably used for a use in a sensor etc.

The nucleic-acid-responsive gel of the present invention is a gel which changes its volume in response to a specific nucleic acid. More specifically, the nucleic-acid-responsive gel is a gel which swells by absorbing a liquid upon recognition of a specific nucleic acid. A volumetric change of the nucleic-acid-responsive gel of the present invention is reversible. This makes it possible to use the nucleic-acid-responsive gel repeatedly. As a result, it is possible to use the nucleic-acid-responsive gel as a sensor material having a further better reproducibility.

A volumetric change of the nucleic-acid-responsive gel of the present invention is not particularly limited which is caused upon recognition of a nucleic acid. A swelling ratio, which is a value obtained by dividing a volume after the volumetric change by a volume before the volumetric change, is preferably 1.02 or higher, or, more preferably 1.1 or higher. A higher swelling ratio is preferable because it gives the nucleic-acid-responsive gel a higher sensitivity. An upper limit of the swelling ratio of the nucleic-acid-responsive gel of the present invention varies depending on an amount of cross-linkages introduced in the network structure, a type of a polymer compound, a type of a solvent, a state of a dissociable group in a polymeric chain, etc. Usually, the upper limit is approximately 2. Note that, in a case where the nucleic-acid-responsive gel has a cylindrical shape, "Swelling ratio" refers to a ratio obtained by a method shown in Examples to be described later. Examples herein show a method for finding a swelling ratio of the nucleic-acid-responsive gel having a cylindrical shape. However, in a case where the nucleic-acid-responsive gel has a spherical shape for example, a swelling ratio is worked out based on a diameter of the spherical shape, instead of "a diameter of a cylindrical shape" used in Examples herein.

The nucleic-acid-responsive gel of the present invention may be arranged to include (i) fine particles such as silica particles, (ii) a color material, or (iii) molecules having a fluorescent chromophore group. The use of the nucleic-acid-responsive gel with this arrangement makes it possible to easily detect a volumetric change of the nucleic-acid-responsive gel and a strand exchange between nucleic acids visually or by using a spectroscope, a fluorescence microscope, or the like.

In the nucleic-acid-responsive gel of the present invention, in the presence of another nucleic acid which forms a more stable double strand in combination with any one of the two single-stranded nucleic acids hybridized with each other which form the probe, or which competitively hybridizes with any one of the two single-stranded nucleic acids hybridized with each other, another nucleic acid replaces the other one of the two single-stranded nucleic acids hybridized with each other. A strand exchange thus occurs. This accordingly causes a decrease in cross-link density. As a result, the nucleic-acid-responsive gel swells. Therefore, the nucleic-acid-responsive gel can be used for detection of a target nucleic acid. A probability of a strand exchange is determined by a balance between (i) a strength of hydrogen bond between the two single-stranded nucleic acids bound with the polymer compound constituting the network structure of the polymer gel, and (ii) a strength of hydrogen bond formed by a strand exchange occurred between the target nucleic acid and any one of the two single-stranded nucleic acids. Accordingly, it is considered that the difference between the swelling behavior occurred in a case where the probe had one or more base mismatches and that occurred in a case where the probe had no base mismatch was brought about by a slight difference between strengths of hydrogen bonds of the probes. Further, it is possible to change a strength of the hydrogen bond of a probe which forms cross-linking points, by changing the combination of two single-stranded nucleic acids bound with the polymer compound. This makes it possible to control easiness of a strand exchange. This allows flexible design of a nucleic acid recognition response behavior of the nucleic-acid-responsive gel of the present invention.

(II) Method for Producing Nucleic-acid-responsive Gel

A method for producing the nucleic-acid-responsive gel of the present invention is not particularly limited, but may be any method, provided that the hybridized probe can be chemically bound with the network structure of the gel so as to form a cross-linkage.

Examples of a method for producing the nucleic-acid-responsive gel of the present invention encompass a method for producing a nucleic-acid-responsive gel, including: (a) introducing a reactive functional group to two single-stranded nucleic acids to be hybridized with each other; (b) forming a double strand as a probe by hybridizing the two single-stranded nucleic acids having the reactive functional group introduced in the step (a); and (c) copolymerizing, in presence or absence of a cross-linking agent, the probe obtained in the step (b) with a monomer which forms a polymer gel.

In the step (a), a reactive functional group is introduced to the two single-stranded nucleic acids. The reactive functional group used in the step is not particularly limited, provided that it is a group capable of chemically bonding with the polymer compound constituting the network structure of a polymer gel. Examples of the reactive functional group are a vinyl group, a (meth)acryloyl group, a hydroxyl group, a carboxyl group, and an amino group. A position in each single-stranded nucleic acid where a reactive functional group is introduced is not also particularly limited. From a viewpoint of ease of the introduction of the reactive functional group, it is preferable to introduce the reactive functional group to each of 5' terminals of the two single-stranded nucleic acids to be hybridized, or to introduce a reactive functional group to each of 3' terminals of the two single-stranded nucleic acids. It follows that the probe formed of the two single-stranded nucleic acids hybridized with each other has the functional reactive groups at its both ends. Although a reactive functional group is preferably introduced to a 5' terminal or a 3' terminal, a position where a reactive functional group is introduced is not limited to this, but may be any position, provided that the probe formed of the two single-stranded nucleic acids hybridized with each other is fixed with the network structure of the polymer gel so that the two strands form a cross-linkage.

A method for introducing a reactive functional group is not also particularly limited, but may be a conventional method. Examples of a method for introducing, e.g., a vinyl group encompass a method in which a single-stranded nucleic acid having an aminated terminal is reacted with N-succinimidyl acrylate.

The step (b) can be performed by, e.g., mixing respective solutions of the two single-stranded nucleic acids having the reactive functional group thus introduced, at a temperature lower than the one at which the double-stranded nucleic acids (two single-stranded nucleic acids hybridized with each other) are dissociated from each other.

In the step (c), the probe thus obtained and a monomer are copolymerized in the presence or absence of a cross-linking agent, thereby obtaining the nucleic-acid-responsive gel. A description of the monomer is omitted because it is the same as that of (I) above. A description of the cross-linking agent used in the step (c) is omitted because it is also the same as that of (I) above. Although the step (c) is preferably performed in the presence of the cross-linking agent, the step (c) can be performed in the absence of the cross-linking agent. In the case of the absence of the cross-linking agent, it is possible to obtain a nucleic-acid-responsive gel cross-linked only by the probe.

In the step (c), the probe can be copolymerized with another monomer other than the aforementioned monomers and the aforementioned cross-linking agents which are used if necessary. Such another monomer is not particularly limited, provided that it does not adversely affect an ability of a nucleic-acid-responsive gel to be obtained.

The method of polymerization is not particularly limited, but can suitably be radical polymerization, ion polymerization, polycondensation, ring-opening polymerization, or the like. Suitable examples of a solvent which can be used in the polymerization encompass water, a phosphate buffer solution, a Tris buffer solution, an acetate buffer solution, methanol, and ethanol.

A polymerization initiator used in the step (c) is not also particularly limited, but can suitably be, e.g., a persulfate such as ammonium persulfate or sodium persulfate; hydrogen peroxide; a peroxide such as t-butylhydroperoxide or cumene hydroperoxide; azobisisobutyronitrile; benzoyl peroxide; or the like. Among them, a polymerization initiator which shows a oxidizing capability, such as a persulfate or a peroxide, can also be used as a redox initiator in combination with, e.g., sodium bisulfite or N,N,N'N'-tetramethylethylenediamine.

A polymerization temperature is not particularly limited, but is preferably a temperature in a range in which the two single-stranded nucleic acids introduced as a probe are not dissociated from each other. A polymerization temperature in such a range makes it possible to bind the two single-stranded nucleic acids with the network structure of the gel while maintaining its stable double strand. A time for polymerization is not also particularly limited, but is usually in a range from 4 hours to 48 hours.

Respective concentrations of a monomer, a cross-linking agent, etc. are not particularly limited, provided that a polymer gel can be obtained. A concentration of the polymerization initiator is not also particularly limited, but can be suitably chosen.

The nucleic-acid-responsive gel of the present invention is obtained by removing an unreacted monomer, a cross-linking agent, a solvent, etc. from a reactant mixture obtained in the step (c). A method for removing an unreacted monomer, a cross-linking agent, a solvent, etc. from the reactant mixture is not particularly limited. Examples of the method encompass a method in which a nucleic-acid-responsive gel thus obtained is washed with a nearly neutral buffer solution. Although the nucleic-acid-responsive gel of the present invention is preferably a hydrogel or an organogel, it can be a gel in the dried state. A dried gel obtained by drying the nucleic-acid-responsive gel of the present invention can be obtained by, e.g., freeze-drying a washed nucleic-acid-responsive gel.

Another example of a method for producing the nucleic-acid-responsive gel of the present invention is a method for producing a nucleic-acid-responsive gel, including: (a) introducing a reactive functional group in two single-stranded nucleic acids to be hybridized with each other; (b) forming a double strand as a probe by hybridizing the two single-stranded nucleic acids having the reactive functional group introduced in the step (a); (c) binding the probe obtained in the step (b) with a polymer compound; and, (d) cross-linking, by reaction with a cross-linking agent, the polymer compound obtained in the step (c), so that the polymer compound has a network structure.

The steps (a) and (b) are not explained here repeatedly because they are the same as those of the aforementioned method for producing the nucleic-acid-responsive gel.

The step (c) makes the probe obtained in the step (b) to bind with the polymer compound. The polymer compound with which the probe binds is not particularly limited, provided that a polymer gel can be obtained by cross-linking the polymer compound. For example, any polymer compound listed in (I) above can be suitably used in the step. The polymer compound with which the probe binds does not have to have the network structure, but alternatively may have a straight-chain structure, a branching structure, or the like. The polymer compound may also be the one having the network structure as long as the probe can bind with the polymer compound. A method for binding the probe with the polymer compound is not particularly limited, but can suitably be a conventional method.

The step (d) makes the polymer compound with which the probe is bound to react with a cross-linking agent, thereby forming the network structure. The cross-linking agent can suitably be any one described in (I) above. Conditions of a cross-linking reaction can be suitably chosen according to types etc. of a polymer compound and a cross-linking agent.

The method described above can be suitably adopted as the method for producing the nucleic-acid-responsive gel of present invention. Accordingly, the nucleic-acid-responsive gel of the present invention encompasses (i) a nucleic-acid-responsive gel obtained by copolymerizing a probe with the monomer in presence or absence of a cross-linking agent, the probe being formed of two single-stranded nucleic acids hybridized with each other each having a reactive functional group, and (ii) nucleic-acid-responsive gel obtained by a process including: (a) binding a probe formed of two single-stranded nucleic acids hybridized with each other each having a reactive functional group, with the polymer compound; and (b) reacting a resultant obtained in the step (a) with a cross-linking agent, so that the resultant has a network structure. More preferably, the monomer in (i) is a monomer including at least one monomer selected from the group consisting of (meth)acrylamide, (meth)acrylic acid, 2-hydroxyethyl (meth)acrylate, alkyl (meth)acrylate, N,N'-dimethyl (meth)acrylamide, N-isopropyl (meth)acrylamide, vinyl acetate, and allylamine. Moreover, more preferably, the polymer compound in (b) is at least one polymer compound selected from the group consisting of poly(meth)acrylamide, poly (meth)acrylic acid, polyalkyl (meth)acrylate, poly-2-hydroxyethyl methacrylate, poly-N,N'-dimethyl (meth)acrylamide, poly-N-isopropyl (meth)acrylamide, polyvinyl alcohol, polyallylamine, cellulose, chitosan, alginic acid, and derivatives thereof.

The method described above can be suitably adopted as the method for producing the nucleic-acid-responsive gel of the present invention. Furthermore, the method of the present invention can be, e.g., a method in which a polymer gel is synthesized by polymerizing a monomer, and then, two single-stranded nucleic acids hybridized with each other are caused to bind with the network structure of the polymer gel.

The method for producing the nucleic-acid-responsive gel of the present invention may include a step of designing a probe. In the step, two single-stranded nucleic acids which form a probe can be designed in accordance with a nucleic acid to be detected. In the case of, e.g., detection of a single nucleotide polymorphism, a probe is formed of (i) a single-stranded nucleic acid which is completely complementary to the base sequence having the single nucleotide polymorphism (SNP), and (ii) a single-stranded nucleic acid which hybridizes with (i) while having one or more base mismatches.

(III) Use of Nucleic-Acid-Responsive Gel (III-1) Method for Detecting Nucleic Acid by Using Nucleic-Acid-Responsive Gel The nucleic-acid-responsive gel of the present invention swells in the presence of a target nucleic acid which causes a strand exchange between two single-stranded nucleic acids by hybridizing with any one of the two single-stranded nucleic acids fixed inside the network structure of a polymer gel. Therefore, the nucleic-acid-responsive gel of the present invention can be used for detection of a target nucleic acid. Accordingly, the present invention encompasses a method for detecting a nucleic acid by using the nucleic-acid-responsive gel of the present invention. The nucleic-acid-responsive gel of the present invention changes its volume not only when a more stable double strand is formed as is the case where (i) the target nucleic acid is completely complementary to a hybridized part of any one of the two single-stranded nucleic acids, or (ii) the target nucleic acid is more homologous with any one of the two single-stranded nucleic acids than with the other one, but also when an equally stable double strand is formed. Therefore, the probe can be designed in accordance with a nucleic acid to be detected. In the present Description, "target nucleic acid" refers to a nucleic acid which causes the nucleic-acid-responsive gel of the present invention to change its volume in response to the nucleic acid.

A method of the present invention for detecting a target nucleic acid, includes: contacting a nucleic-acid-responsive gel with a specimen containing a nucleic acid; and detecting, from a volumetric change of the nucleic-acid-responsive gel, whether or not a strand exchange is caused by the target nucleic acid.

The nucleic acid and the target nucleic acid contained in the specimen may be DNA, RNA, or PNA. The nucleic acid and the target nucleic acid each may be a single-stranded or double-stranded nucleic acid. The specimen containing the target nucleic acid is not limited to a solution such as water containing a nucleic acid or a buffer solution containing a nucleic acid, provided that it is possible to detect a target nucleic acid by using the nucleic-acid-responsive gel of the present invention. Examples of the specimen encompass blood and other bodily fluids containing genes.

In the step of contacting the nucleic-acid-responsive gel of the present invention with the specimen containing a nucleic acid, a temperature at which the step is performed is not particularly limited, but can be the one adjusted according to a desired detection accuracy.

In the present Description, "detection accuracy" means detection sensitivity and selectivity of a base sequence of a nucleic acid to be detected.

That is, it is possible to control detection sensitivity and/or selectivity of a base sequence of a nucleic acid to be detected, by adjusting a temperature at which the step of contacting the nucleic-acid-responsive gel with a specimen containing the nucleic acid.

This utilizes knowledge that a temperature affects (i) a swelling ratio of the nucleic-acid-responsive gel of the present invention brought into contact with a target nucleic acid, and (ii) a balance between (I) the hydrogen bond of a probe and (II) the hydrogen bond between a target nucleic acid and any one of the two single-stranded nucleic acids which form the probe.

Figure 7:
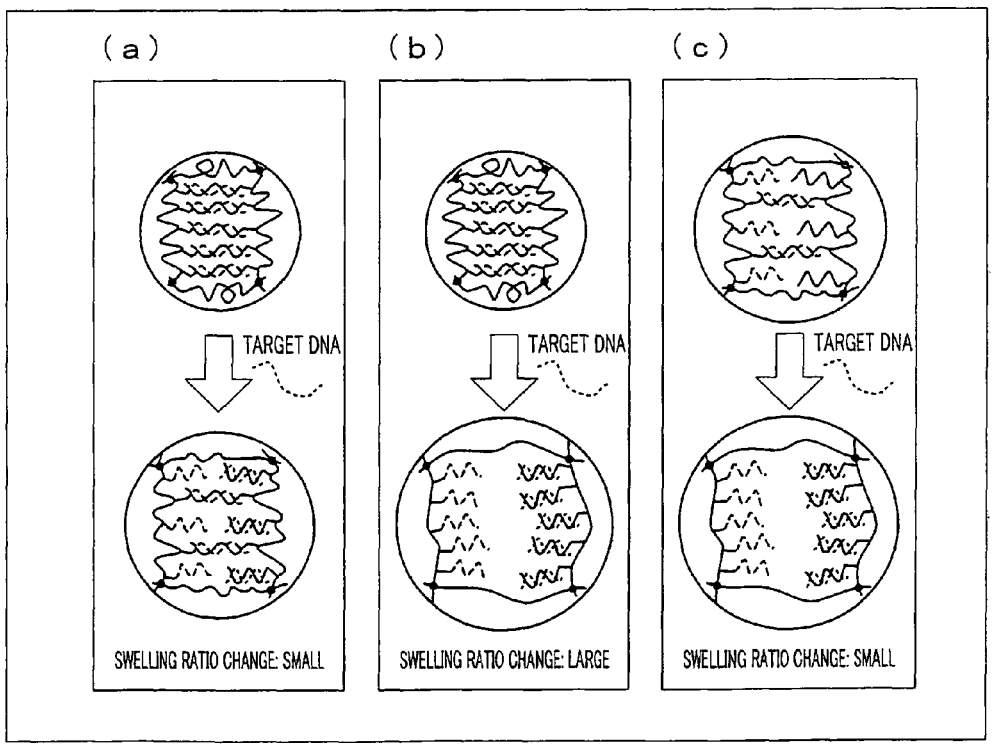
FIGS. 7(a)-7(c) show a view schematically illustrating a mechanism by which the nucleic-acid-responsive gel brought into contact with a target nucleic acid shows different swelling ratios depending on temperatures.

In view of this, the following explains how a swelling ratio depends on a temperature, with reference to FIG. 7. FIG. 7 is a view schematically illustrating a mechanism by which the nucleic-acid-responsive gel of the present invention brought into contact with a target nucleic acid shows different swelling ratios depending on temperatures. (a) of FIG. 7 illustrates a case where the nucleic-acid-responsive gel is brought into contact with a target nucleic acid under low temperature; (b) of FIG. 7 illustrates a case where the temperature is adjusted so that the nucleic-acid-responsive gel has the highest responsiveness; (c) of FIG. 7 illustrates a case where the temperature is high.

Hereinafter, "swelling ratio change" refers to a change in swelling ratio caused by a response of the nucleic-acid-responsive gel of the present invention to a target nucleic acid. Specifically, the swelling ratio change can be calculated as a difference between (i) a swelling ratio measured when the nucleic-acid-responsive gel of the present invention is soaked in a solution of the target nucleic acid and (ii) a swelling ratio measured when the nucleic-acid-responsive gel is soaked in a buffer solution containing no target nucleic acid.

In general, the hydrogen bond between two strands of DNA is highly stable under a low temperature. Accordingly, in a case where the nucleic-acid-responsive gel of the present invention is brought into contact with a target nucleic acid under low temperature, the swelling ratio change is small as shown in (a) of FIG. 7 because a strand exchange is unlikely to occur between the target nucleic acid and the probe.

In the case of a high temperature, generally, the hydrogen bond between two strands of DNA is likely to be dissociated. Accordingly, in a case where the nucleic-acid-responsive gel of the present invention is brought into contact with the target nucleic acid at high temperature, cross-linkages are decreased because a part of probes are dissociated as illustrated in (c) of FIG. 7 even in the absence of the target nucleic acid. In other words, a swelling ratio of the nucleic-acid-responsive gel of the present invention increases before the nucleic-acid-responsive gel is brought into contact with the target nucleic acid. Further, the hydrogen bond is unlikely to be formed between any one of the two single strands of DNA and the target DNA due to a high temperature. As a result, a swelling ratio change is small even if the target nucleic acid is hybridizable with the probe by contacting with the nucleic-acid-responsive gel.

On the other hand, for the nucleic-acid-responsive gel of the present invention, there is a temperature at which the aforementioned decrease in the swelling ratio change is suppressed so that the swelling ratio change becomes largest. As illustrated in (b) of FIG. 7, a strand exchange is likely to occur because the hydrogen bond of the probe is not excessively stable. In addition, the nucleic-acid-responsive gel does not swell before the target nucleic acid is brought into contact with the nucleic-acid-responsive gel because the hydrogen bond of the probe is not unstable. Furthermore, the target nucleic acid and any one of the two single strands of DNA which form the probe are likely to form hydrogen bond therebetween.

As described above, a temperature at which a specimen is brought into contact with the nucleic-acid-responsive gel is closely related to a balance between (i) the stability (melting temperature) of the hydrogen bond formed between the two single strands of the nucleic acid which form the probe, i.e., the stability (melting temperature) of the hydrogen bond formed between the two single-stranded nucleic acids introduced as cross-linking points and (ii) the stability (melting temperature) of the hydrogen bond formed between the target nucleic acid and any one of the two single-stranded nucleic acids. The temperature is also closely related to the swelling ratio change.

Therefore, it is possible to control detection accuracy by adjusting, on the basis of the aforementioned balance of the stability of the hydrogen bond and the swelling ratio change, a temperature for performing the step of contacting the nucleic-acid-responsive gel with a specimen containing a nucleic acid.

For example, it is possible to increase detection sensitivity by adjusting the temperature at which the nucleic-acid-responsive gel is brought into contact with the specimen containing the nucleic acid, toward the temperature at which the swelling ratio change becomes largest. In addition, it is possible to decrease the detection sensitivity by adjusting the temperature at which the nucleic-acid-responsive gel is brought into contact with a specimen containing a nucleic acid, away from the from the temperature at which the swelling ratio change becomes largest.

In other words, it is possible to control the detection sensitivity by adjusting, with reference to the temperature at which the swelling ratio change becomes largest, the temperature for performing the step of contacting the nucleic-acid-responsive gel into contact with the specimen containing the nucleic acid.

It is also possible to control selectivity of a base sequence of the nucleic acid to be detected, by adjusting the temperature for performing the step of contacting the nucleic-acid-responsive gel with the specimen containing the nucleic acid, in such a manner that the temperature is adjusted between (i) a melting temperature of the hydrogen bond formed between the two single-stranded nucleic acids which form the probe and (ii) a melting temperature of the hydrogen bond formed between (I) any one of the two single-stranded nucleic acids which is intended to hybridize with the target nucleic acid and (II) the nucleic acid having a base sequence which is completely complementary to (I).

Assume for example that, in the nucleic-acid-responsive gel, the probe has, between the two single-stranded nucleic acids which form the hydrogen bond, a "N" number of sites where respective normal base pairs are not formed (hereinafter, such sites are referred to as "base mismatch"). Assume that a melting temperature of the hydrogen bond is $T_N$° C. Also, assume that $T_n$° C. is a melting temperature of hydrogen bond between (i) any one of the two single-stranded nucleic acids which is intended to hybridize with a target nucleic acid and (ii) a nucleic acid having a base sequence which is completely complementary to (i). Assume T is a temperature for actually performing detection.

In general, $T_n > T_N$ holds. By setting T to a temperature which is in a range from $T_N$ to $T_n$ and is close to $T_n$, it becomes possible to detect a nucleic acid having few base mismatches in relation to the single-stranded nucleic acid intended to hybridize with the target nucleic acid. By setting T to a temperature which is in a range from $T_N$ to $T_n$ and is close to $T_N$, it is possible to detect a nucleic acid having many base mismatches in relation to the single-stranded nucleic acid.

By adjusting T in the range from $T_N$ to $T_n$, it is possible to control the selectivity of a base sequence of the nucleic acid to be detected. If the respective melting temperatures $T_N$ and $T_n$ of the two types of hydrogen bond vary depending on whether or not the two single-stranded nucleic acids etc. are contained in the nucleic-acid-responsive gel, T is adjusted on the basis of the respective melting temperatures of the two types of hydrogen bond formed in the nucleic-acid-responsive gel. In many cases, an upper limit of the number of base mismatches between the single-stranded nucleic acid and the nucleic acid to be detected is N−1. Depending on conditions such as the base sequences of the single-stranded nucleic acid etc., and a temperature, the upper limit can be N or more.

A temperature range for the detection is not particularly limited. Within a temperature range from 0° C. to 60° C., the nucleic-acid-responsive gel of the present invention can appropriately swell upon contact with a target nucleic acid.

It is possible to control the detection accuracy by thus adjusting the temperature for performing the step of contacting the nucleic-acid-responsive gel with a specimen containing a nucleic acid. For example, in a case where the nucleic-acid-responsive gel of the present invention is used for detection of a SNP, it is possible to improve selectivity of a base sequence of a nucleic acid to be detected, by performing the detection at a temperature which is in a range from $T_N$ to $T_n$ and is close to $T_n$.

How to measure a volumetric change of the nucleic-acid-responsive gel so as to detect whether or not a strand exchange due to a target nucleic acid occurs is not particularly limited, but the measurement can be performed by a conventional method for detecting a volumetric change of a stimuli-responsive gel. Examples of such a method encompass: a method in which a volumetric change is observed by a microscope; a method in which fine particles such as silica particles are arrayed in a nucleic-acid-responsive gel, and a change in wavelength of a structural color and a change in intensity thereof are measured; a method in which a color material is dispersed in a nucleic-acid-responsive gel, and an optical transmittance is measured; and a method in which molecules having a fluorescent chromophore group are introduced in a nucleic-acid-responsive gel, and a fluorescence intensity is measured.

Whether or not a strand exchange due to a target nucleic acid occurs can be also detected by detecting a weight change of the nucleic-acid-responsive gel caused by the hybridization of the target nucleic acid, in addition to the aforementioned method in which the volumetric change is detected. Whether or not a strand exchange due to a target nucleic acid occurs can also be detected by a method in which the nucleic acids which serve as the probe fixed inside the network structure are labeled with a fluorescent substance etc. in advance, and the strand exchange is detected by a spectroscope etc.

(III-2) Nucleic Acid Detection Kit

The present invention that is related to the use of the nucleic-acid-responsive gel encompasses, not only the aforementioned method for detecting a nucleic acid, but also a nucleic acid detection kit for carrying out the method. Specifically, the nucleic acid detection kit of the present invention includes at least the nucleic-acid-responsive gel of the present invention.

The nucleic acid detection kit may further include a comparative specimen (nucleic acid etc.) or the like which is used as a control, a buffer of various kinds, or the like.

The use of the nucleic acid detection kit makes it possible to carry out easily and simply the method of the present invention for detecting a nucleic acid. This allows the application of the present invention at the level of industries such as the clinical testing industry and the pharmaceutical industry.

Moreover, the use of the present invention makes it possible to detect or identify a target nucleic acid with high sensitivity and ease. Therefore, the present invention is also applicable to: medical treatment, prevention, and diagnosis of diseases due to DNA damage; DNA sequence analysis in scientific technological research; and the like.

(III-3) Nucleic Acid Detection Apparatus

By fixing the nucleic-acid-responsive gel of the present invention with a sensor capable of detecting a volumetric change of a gel caused by swelling of the gel, it becomes possible to make a nucleic acid detection apparatus capable of detecting a target nucleic acid easily and surely by using the sensor.

More specific examples of the nucleic acid detection apparatus encompass the one in which the nucleic-acid-responsive gel of the present invention is fixed onto the surface of a minute sensor chip which is connected with a measurement apparatus which measures the volumetric change of the nucleic-acid-responsive gel caused by the swelling thereof and displays a measurement result. With the use of the nucleic acid detection apparatus, the target nucleic acid can be specifically detected by just contacting a specimen containing the target nucleic acid with the surface of the sensor chip for detection.

The measurement apparatus with which the sensor chip is connected is not particularly limited, but can suitably be a conventional one. For example, the measurement apparatus may be a film thickness measurement apparatus. In the case of the film thickness measurement apparatus, the target nucleic acid can be detected by measuring, as a change in film thickness, a volumetric change of the nucleic-acid-responsive gel caused in response to the target nucleic acid in the specimen.

The measurement apparatus may be a weighing scale. In this case, the nucleic-acid-responsive gel increases in its weight and swells when a specimen containing a target nucleic acid is brought into contact with the surface of the sensor chip for detection. The nucleic-acid-responsive gel increases in its weight and swells for the reason that the target nucleic acid is taken into the nucleic-acid-responsive gel. The volumetric change of the nucleic-acid-responsive gel caused by the swelling depends on an amount of the target nucleic acid taken into the nucleic-acid-responsive gel and a weight of the nucleic-acid-responsive gel containing the target nucleic acid. Accordingly, a target nucleic acid can be detected by measuring a weight change of the nucleic-acid-responsive gel caused by the intake of the target nucleic acid.

In the case of use of the aforementioned nucleic-acid-responsive gel labeled with fine particles such as silica particles; a color material; molecules having a fluorescent chromophore group; or the like, a spectroscope for example can be used as the measurement apparatus.

The apparatus with which the sensor chip is connected is not limited to the aforementioned measurement apparatus which measures a volumetric change and displays a measurement result, but can be an apparatus for measuring another type of amount except the volumetric change, provided that the apparatus is capable of detecting a strand exchange between nucleic acids.

EXAMPLES

Example 1

Production of Nucleic-Acid-Responsive Gel

<Synthesis of Vinyl-Group-Introduced Oligo DNA>

As shown by the reaction formulas in FIG. 1, a vinyl group was introduced to each strand of oligo DNA having aminated 5' terminal.

First, 1 mg (0.35 µmol) of oligo DNA having aminated 5' terminals (3'-CCGGTCGCG-5'-$(CH_2)_6NH_2$, Tsukuba Oligo Service Co., Ltd.) was dissolved in 500 µl of a carbonate buffer solution (pH 9.0). Into a resultant solution thus obtained, 5 mg (30 µmol) of N-succinimidyl acrylate (NSA) dissolved in 50 µl of dimethylformamide (DMF), 1.5 mg (14 µmol) of hydroxynone dissolved in 10 µl of DMF, and further, 400 ml of pure water were added. Then, the resultant solution was stirred overnight at room temperature. A reaction liquid thus obtained was fractionated by gel filtration chromatography (Sephadex G-25) so that unreacted NSA and DNA were separated. A DNA fraction thus obtained was concentrated. Then, vinyl-group-introduced DNA and unreacted DNA were separated by isolating them by high-performance liquid chromatography (Wakosil-DNA). A vinyl-group-introduced DNA fraction thus obtained was concentrated. Then, the solvent was exchanged for pure water by gel filtration chromatography (Sephadex G-25). The resultant was concentrated, and then, freeze-dried, thereby obtaining vinyl-group-introduced DNA.

A vinyl group was also introduced by the same method to each strand of oligo DNA having an aminated 5' terminal (3'-CGCGTCCGG-5'-$(CH_2)_6NH_2$, Tsukuba Oligo Service Co., Ltd.)

<Production of Nucleic-Acid-Responsive Gel>

Figure 2:
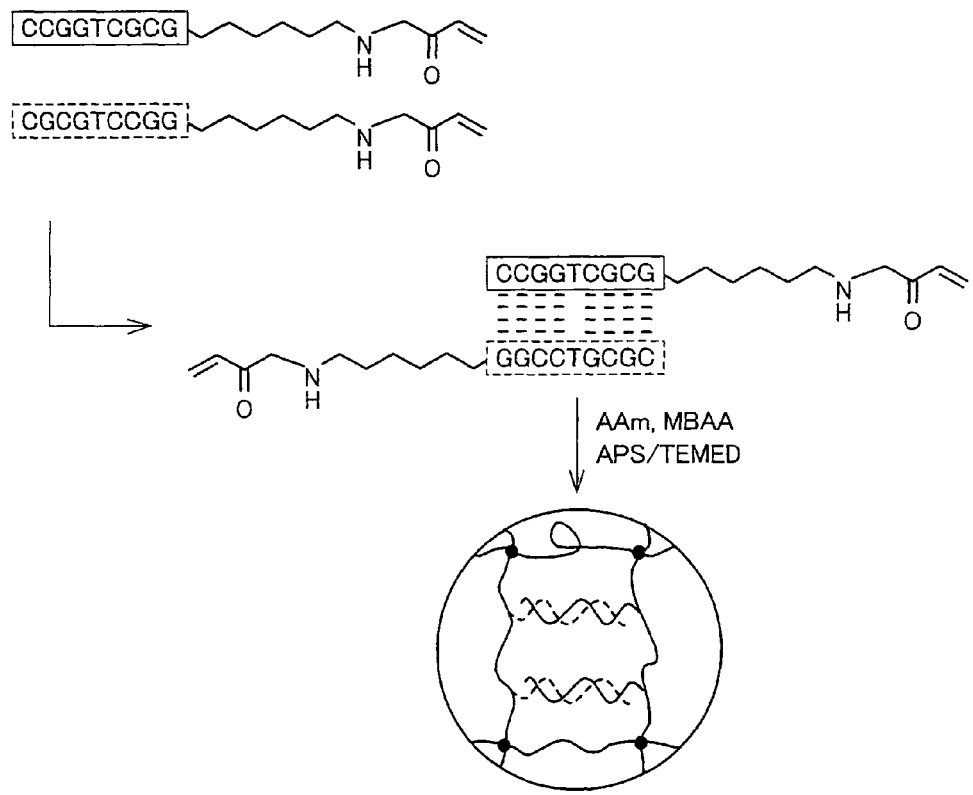
FIG. 2 is a view showing reaction formulas for producing a nucleic-acid-responsive gel in Examples.

Then, as shown by the reaction formula in FIG. 2, a nucleic-acid-responsive gel was produced in which probes each formed of two single strands of the vinyl-group-introduced oligo DNA hybridized with each other were fixed with a network structure of a polymer gel. As shown in FIG. 2, the two single strands of the vinyl-group-introduced oligo DNA were hybridized with each other while having a base mismatch "T-T" in the central base pair.

1 µmol of each of the two types of vinyl-group-introduced DNA synthesized above was dissolved at 5° C. in 10 mM of a Tris-150 mM HCl buffer solution (Tris buffer solution, pH 7.4), thereby forming double strands in the solution. Then, 15 mg (211 µmol) of acrylamide (AAm); 3 µl of 5 mg/ml N,N'-methylenebisacrylamide (MBAA); and 2 µl of 0.1M ammonium persulfate (APS) and 2 µl of 0.8M N,N,N'N'-tetramethylethylenediamine (TEMED) which were used as a redox initiator were added in the solution. The solution was poured into a glass tube having an inside diameter of 1 mm, and polymerization was performed therein at 5° C. for 24 hours, thereby synthesizing a nucleic-acid-responsive gel. Then, the nucleic-acid-responsive gel thus obtained was taken out of the glass tube and washed sufficiently by soaking the nucleic-acid-responsive gel in the Tris buffer solution, thereby removing unreacted monomer etc. from the nucleic-acid-responsive gel. The washed nucleic-acid-responsive gel was cut by a cutter knife so as to have a length of approximately 2 mm. A cylindrical nucleic-acid-responsive gel was thus obtained.

Example 2

Measurement of Swelling Ratio of Nucleic-Acid-Responsive Gel

The nucleic-acid-responsive gel produced in Example 1 was caused to sufficiently swell to reach equilibrium in the Tris buffer solution. Then, the nucleic-acid-responsive gel was soaked at 25° C. in a 0.2 mM DNA solution whose DNA is completely complementary to any one of the two single strands of oligo DNA bound with the nucleic-acid-responsive gel. The DNA solution was prepared by dissolving DNA in the Tris buffer solution so as to have 0.2 mM of DNA concentration. A diameter change of the cylindrical nucleic-acid-responsive gel was measured by an optical microscope (BX51, Olympus Corporation) so that a change brought by swelling was evaluated on the basis of a swelling ratio found by the following equation.

$$\text{Swelling ratio} = (d/d_0)^3 \qquad (1)$$

$d_0$ represents a diameter (cm) of the cylindrical shape of the nucleic-acid-responsive gel in the Tris buffer solution which diameter was measured before the nucleic-acid-responsive gel was soaked in the DNA solution (hereinafter, the nucleic-acid-responsive gel is referred to as "nucleic-acid-responsive gel in the Tris buffer solution"); d represents a diameter (cm) of the cylindrical shape of the nucleic-acid-responsive gel in the DNA solution which diameter was measured while the nucleic-acid-responsive gel was soaked in the DNA solution (hereinafter, the nucleic-acid-responsive gel is referred to as "nucleic-acid-responsive gel in the DNA solution"). As a control, another same measurement was performed on a polyacrylamide (PAAm) gel synthesized in the same manner as that of Example 1 except that the vinyl-group-introduced oligo DNA was not bound with the polyacrylamide gel. A diameter of each cylindrical shape was obtained by measuring by an optical microscope a side-to-side width of each cylindrical nucleic-acid-responsive gel.

Figure 3:
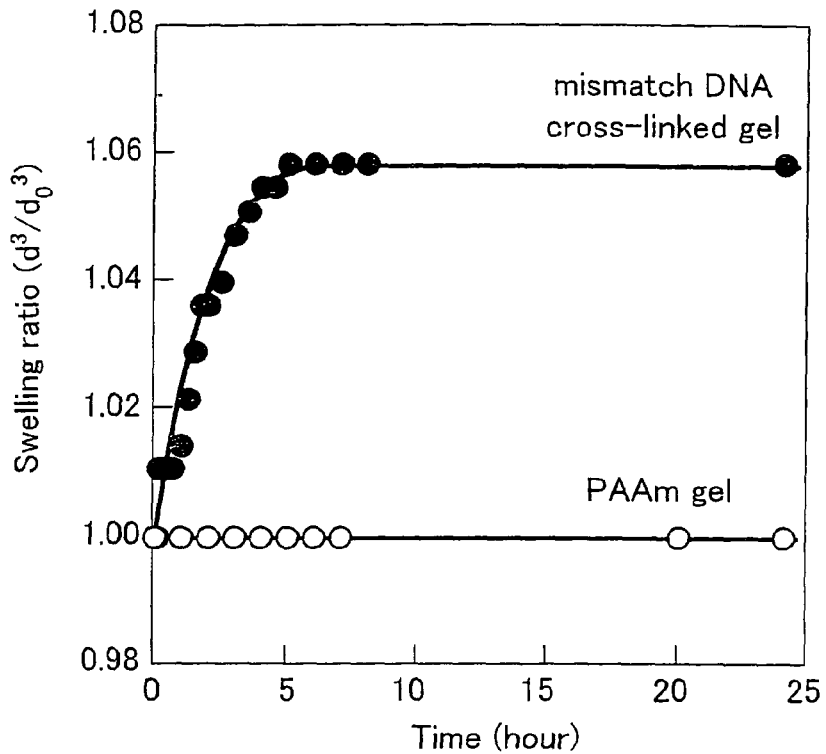
FIG. 3 is a graph showing changes in swelling ratio of the nucleic-acid-responsive gel and a polyacrylamide (PAAm) gel which was a control. The changes in swelling ratio were found while the gels were soaked in a solution of completely complementary DNA (Target DNA: 3'-GGCCAGCGC-5').

FIG. 3 shows the swelling ratio changes of the nucleic-acid-responsive gel and the polyacrylamide (PAAm) gel which was the control. The swelling ratio changes were measured while the gels were soaked in a solution of completely complementary DNA (Target DNA: 3'-GGCCAGCGC-5'). In FIG. 3, the vertical axis of the graph represents swelling ratios; the horizontal axis represents soaking time (unit: hour); the black circles represent swelling ratios of the nucleic-acid-responsive gel; the white circles represent swelling ratios of the polyacrylamide (PAAm) gel. As shown in FIG. 3, the PAAm gel hardly changed in swelling ratio while the nucleic-acid-responsive gel increased in swelling ratio with time, i.e., showed response to a nucleic acid.

Example 3

Measurement of Cross-Link Density of Nucleic-Acid-Responsive Gel

Respective compressive elastic moduli of the nucleic-acid-responsive gel produced in Example 1 and the polyacrilamide (PAAm) gel were measured by a compression testing machine (EZ Test 10N, Shimadzu Corporation) in cases where each gel was soaked in the Tris buffer solution and the DNA solution each. Then, a cross-link density ye of the nucleic-acid-responsive gel was found by the following equation:

$$G = R \cdot T \cdot v_e v_2^{1/3}$$

where G is a compressive elastic modulus (Pa); R is the gas constant; T is an absolute temperature; $v_e$ is a cross-link density (mol/m$^3$); $v_2$ is a volume fraction of the polymer compound with which the probes were fixed, with respect to the whole nucleic-acid-responsive gel (polymer compound with which probes were fixed+solvent).

Table 1 below shows respective cross-link densities of the nucleic-acid-responsive gel and the polyacrylamide (PAAm) gel, for cases where each gel was in the Tris buffer solution or the DNA solution.

TABLE 1

| | Cross-link density (mol/m$^3$) in buffer solution | Cross-link density (mol/m$^3$) in DNA solution |
|---|---|---|
| PAAm GEL | 28.57 | 25.69 |
| NAR GEL | 42.92 | 29.18 |

Note:
"NAR Gel" stands for a nucleic-acid responsive gel.

As shown in Table 1, the PAAm gel hardly changed in cross-link density in both the Tris buffer solution and the DNA solution while the nucleic-acid-responsive gel decreased in cross-link density from 42.92 (mol/m$^3$) to 29.18 (mol/m$^3$).

The results of [Example 2] and the present example show that the nucleic-acid-responsive gel swells while its cross-link density decreases in a case where the nucleic-acid-responsive gel is soaked in the DNA solution whose DNA is completely complementary to one of the two single strands of oligo DNA bound with the nucleic-acid-responsive gel. From the results, it is considered that the nucleic-acid-responsive gel swells in response to completely complementary DNA by the mechanism illustrated in FIG. 5. In the nucleic-acid-responsive gel of the present invention, as is illustrated in the left circle in FIG. 5, the two single-stranded nucleic acids hybridized with each other are bound with the network structure of the nucleic-acid-responsive gel so as to form cross-linkage, while the nucleic-acid-responsive gel is soaked in the buffer solution. In the presence of target DNA which is completely complementary to any one of the two single-stranded nucleic acids, a strand exchange occurs (see the right circle in FIG. 5), so that more stable hydrogen bond is formed between the one of the two single-stranded nucleic acids and the target DNA, for the reason that the two single-stranded nucleic acids introduced as cross-linking points are non-complementary by one base to each other. Accordingly, the cross-linking points decrease, thereby causing swelling of the gel.

Example 4

Measurement of Swelling Ratio of Nucleic-Acid-Responsive Gel

A swelling ratio of the nucleic-acid-responsive gel produced in Example 1 was measured in the same manner as that of Example 2. In the measurement, used were three types of 0.2 mM DNA solutions each containing DNA which was non-complementary by one base to one of the two single strands of oligo DNA introduced to the nucleic-acid-responsive gel.

Figure 4:
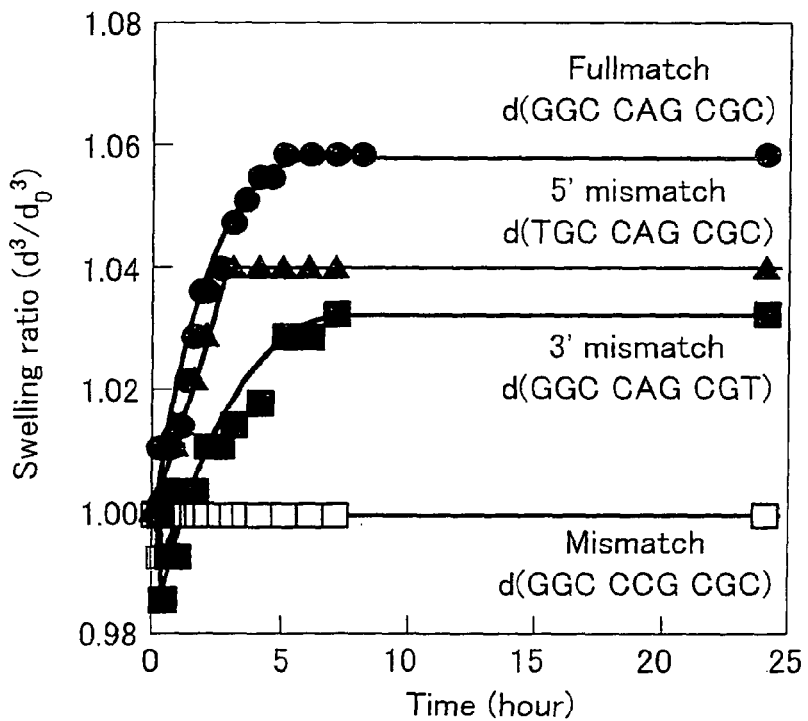
FIG. 4 is a graph showing changes in swelling ratio of the nucleic-acid-responsive gel measured while the nucleic-acid-responsive gel was soaked in three types of DNA solutions which contain three types of DNA, respectively, each having one base mismatch with one of two single strands of the oligo DNA bound with the nucleic-acid-responsive gel.

FIG. 4 shows the measurement result, in combination with a measurement result obtained by use of the completely complementary DNA obtained in Example 2. In FIG. 4, the vertical axis represents swelling ratios; the horizontal axis represents soaking time (unit: hour); the black circles represent a result obtained by using the completely complementary DNA (Target DNA: 3'-GGCCAGCGC-5'); the black triangles represent a result obtained by using DNA which was non-complementary by one base at 5' terminals (Target DNA: 3'-TGCCAGCGC-5'); the black squares represent a result obtained by using DNA which was non-complementary by one base at 3' terminals (Target DNA: 3'-GGCCAGCGT-5'); the white rectangles represent a result obtained by using DNA which was non-complementary by one base in the center of each strand (Target DNA: 3'-GGCCCGCGC-5'). As shown in FIG. 4, the nucleic-acid-responsive gel of the present invention showed different swelling behaviors by recognizing various single nucleotide polymorphisms (SNP). This demonstrates that the nucleic-acid-responsive gel synthesized according to the present invention makes it possible to distinguish the target DNA from another by just observing the volumetric change of the gel caused by one base mismatch.

Example 5

Consideration of Relation Between DNA Content and Swelling Ratio of Nucleic-Acid-Responsive Gel In the present example, swelling ratios of the nucleic-acid-responsive gel were measured with an increased concentration of the oligo DNA contained in the nucleic-acid-responsive gel.

First, vinyl-group-introduced oligo DNA was produced by the method described in Example 1.

Second, the nucleic-acid-responsive gel was produced by the method described in Example 1, except that a concentration of the vinyl-group-introduced oligo DNA was adjusted to $2.4 \times 10^{-1}$ mol % in the dry state of the gel. In the present example, "mol % in the dry state" is a quotient found by dividing the number of moles of the vinyl-group-introduced oligo DNA contained in the nucleic-acid-responsive gel by the number of moles of a residue remaining after the nucleic-acid-responsive gel is dried, i.e., dividing by the total number of moles of AAm and MBAA, which serve as a skeleton of the nucleic-acid-responsive gel, and the vinyl-group-introduced oligo DNA. A concentration of the vinyl-group-introduced oligo DNA contained in the nucleic-acid-responsive gel produced in Example 1 is $4.7 \times 10^{-2}$ mol % in the dry state.

Then, respective swelling ratios of the nucleic-acid-responsive gel produced in the present example, the nucleic-acid-responsive gel produced in Example 1, and the PAAm gel were measured by the method described in Example 2.

Figure 8:
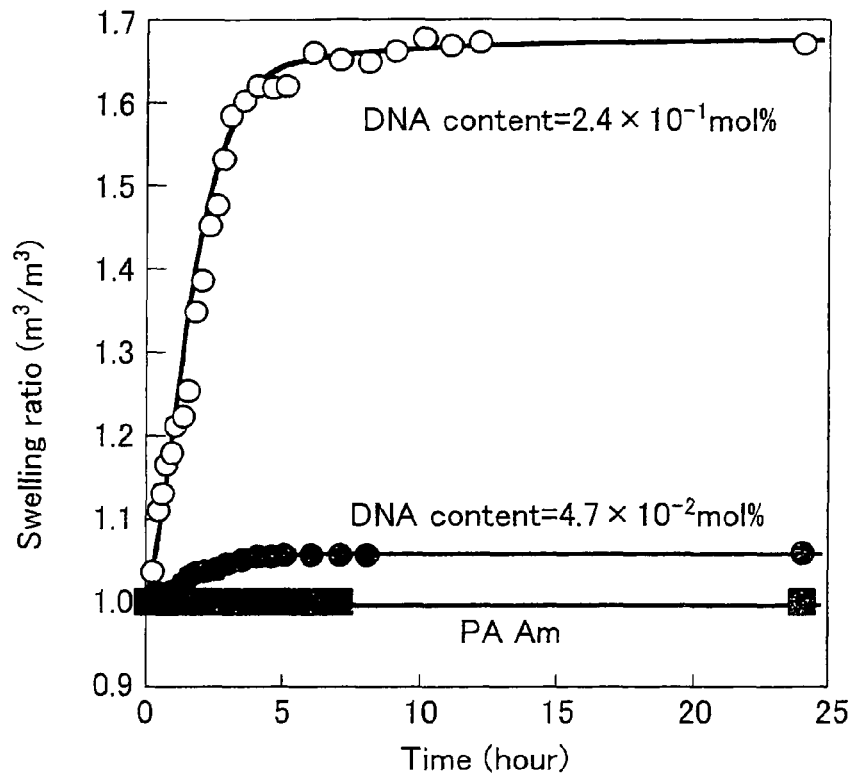
FIG. 8 is a graph showing a change in swelling ratio of the nucleic-acid-responsive gel measured while the nucleic-acid-responsive gel was soaked in the solution of completely complementary DNA.

FIG. 8 shows the measurement result. FIG. 8 is a graph showing swelling ratio changes of the nucleic-acid-responsive gels measured while each gel was soaked in the solution of completely complementary DNA. In FIG. 8, the vertical axis represents swelling ratios; the horizontal axis represents soaking time (unit: hour); the white circles represent swelling ratios of the nucleic-acid-responsive gel produced in the present example; the black circles represent swelling ratios of the nucleic-acid-responsive gel produced in Example 1; the black squares represent swelling ratios of the PAAm gel.

As shown in FIG. 8, a swelling ratio of the nucleic-acid-responsive gel produced in the present example was remarkably higher, i.e., approximately 1.7 times higher than that of the nucleic-acid-responsive gel produced in Example 1. In the nucleic-acid-responsive gel of the present invention, the larger the amount of double strands of DNA which serve as reversible cross-linking points, the larger the change of the number of cross-linking points in the presence of the target DNA. It is considered that this caused the further larger swelling.

The result demonstrates that it is possible to control a response behavior (i.e., swelling ratio) of the nucleic-acid-responsive gel which occurs upon detection of target DNA, by adjusting a DNA content, which serves as a probe, in the nucleic-acid-responsive gel of the present invention.

Example 6

Relation Between Swelling Ratio of Nucleic-Acid-Responsive Gel and Measurement Temperature The present example deals with the relations between measurement temperatures and the nucleic-acid-responsive gel.

In the present example, used was a nucleic-acid-responsive gel produced by the method described in Example 5.

Figure 9:
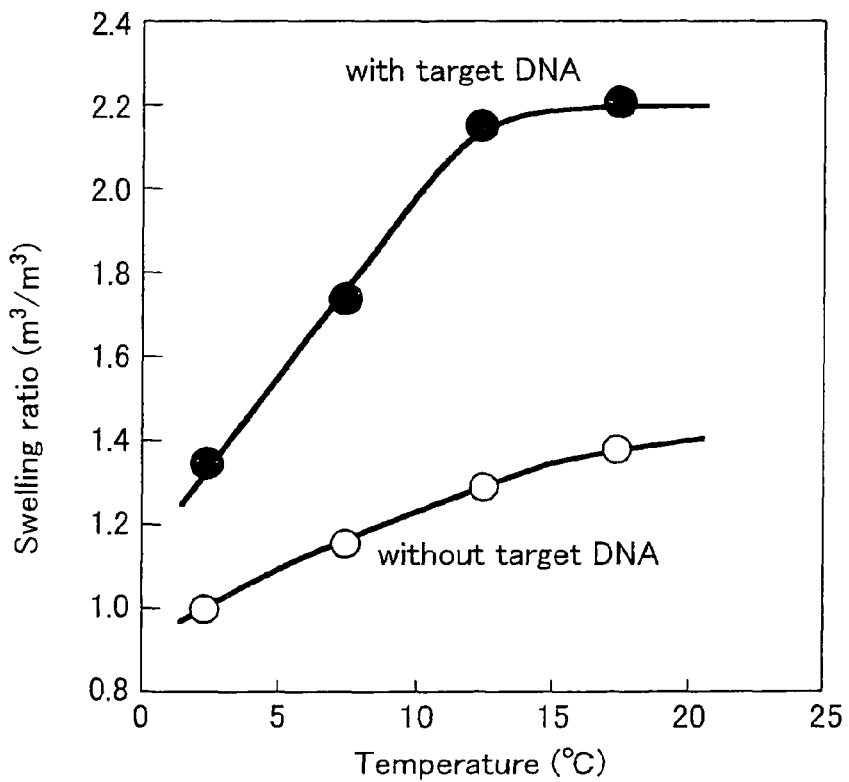
FIG. 9 is a graph showing relations between swelling ratios of the nucleic-acid-responsive gel and measurement temperatures. For comparison, a solution of completely complementary DNA and a buffer solution containing no DNA were used in the measurement.

Measurement of swelling ratios was performed by the method described in Example 2, except for temperature conditions for soaking the nucleic-acid-responsive gel in the solution of completely complementary DNA. In the present example, the measurement was performed under the following four temperature conditions: 5° C., 15° C., 25° C., and 35° C. For comparison, another measurement was performed on the nucleic-acid-responsive gel under the temperature conditions above while the gel was soaked in a buffer solution containing no DNA (i.e., Tris buffer solution). FIG. 9 shows the measurement result obtained after 24 hours from the start of the measurement.

FIG. 9 is a graph showing the relations between swelling ratios of the nucleic-acid-responsive gel and measurement temperatures. For comparison, a solution of completely complementary DNA and a buffer solution containing no DNA were used in the measurement. The vertical axis represents swelling ratios; the horizontal axis represents measurement temperatures (unit: ° C.); the black circles represent swelling ratios of the nucleic-acid-responsive gel soaked in the solution of completely complementary DNA; the white circles represent swelling ratios of the nucleic-acid-responsive gel soaked in the buffer solution containing no DNA.

As shown in FIG. 9, a swelling ratio of the nucleic-acid-responsive gel soaked in the buffer solution containing no DNA also increased with a temperature rise. The reason for the result is considered as below. A double strand of DNA serving as cross-linking points in the nucleic-acid-responsive gel was formed by hydrogen bond. The hydrogen bond was dissociated due to the temperature rise. Accordingly, the double strand of DNA was separated into two single strands of DNA. As a result, a cross-link density decreased, whereby a swelling ratio increased. The temperature dependency of swelling ratios was significant in the case of the solution of completely complementary DNA. That is, a swelling ratio greatly varied depending on a measurement temperature. A difference between swelling ratios caused by the presence or absence of target DNA (i.e., swelling ratio change) indicates a swelling behavior that the nucleic-acid-responsive gel shows in response to the target nucleic acid. The result shows that a swelling behavior is greatly affected by a measurement temperature.

Figure 10:
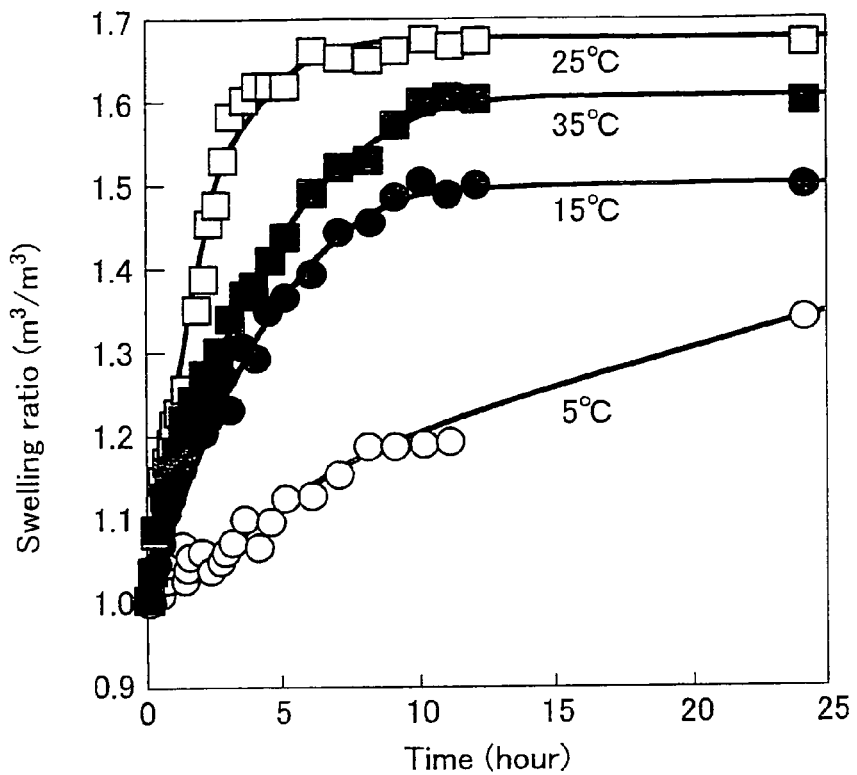
FIG. 10 is a graph showing relations between changes in swelling ratio of the nucleic-acid-responsive gel and measurement temperatures.
Figure 11:
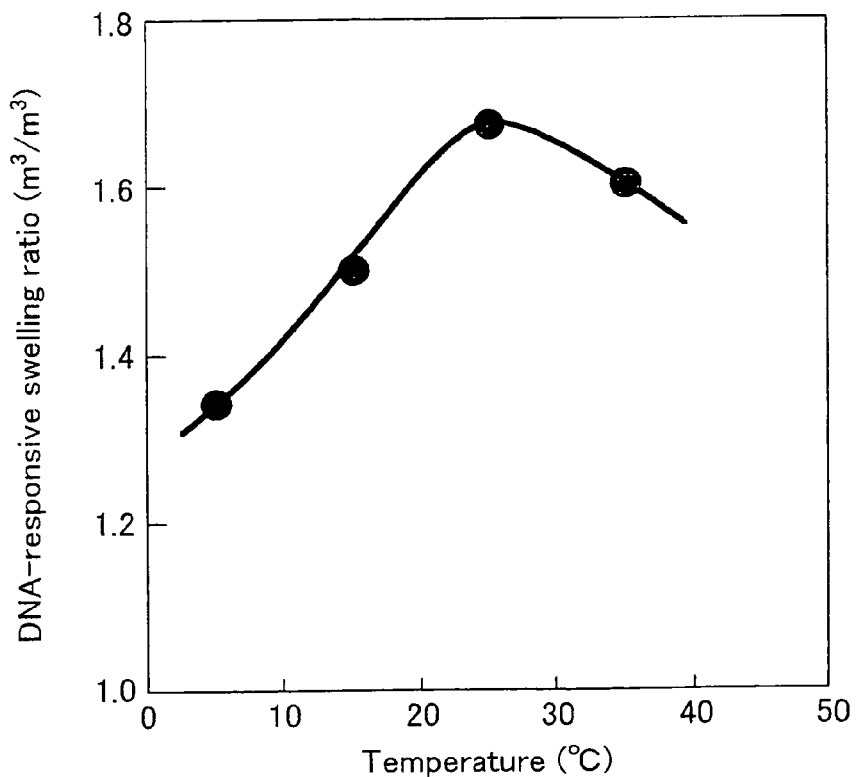
FIG. 11 is a graph showing a relation between swelling ratios of the nucleic-acid-responsive gel and measurement temperatures.

Then, swelling ratio changes were found from the measurement result of the present example, so that relations between swelling ratios and measurement temperatures were considered. FIGS. 10 and 11 show the result.

FIG. 10 is a graph showing relations between swelling ratio changes of the nucleic-acid-responsive gel and measurement temperatures. The vertical axis represents swelling ratios; the horizontal axis represents measurement time (unit: hour); the white circles, black circles, white squares, and black squares represent relations between swelling ratio changes and measurement temperatures: 5° C., 15° C., 25° C., and 35° C., respectively. FIG. 11 is a graph showing relations between swelling ratios of the nucleic-acid-responsive gel which were measured after 24 hours from the start of the measurement and measurement temperatures. The vertical axis represents swelling ratios while the horizontal axis represents measurement temperatures (unit: ° C.).

As shown in FIG. 10, the nucleic-acid-responsive gel swelled in response to the completely complementary DNA at any temperature. As shown in FIGS. 10 and 11, a swelling ratio increased at 25° C. or below with a rise in measurement temperature while a swelling ratio decreased at 25° C. or above. The result indicates that the nucleic-acid-responsive gel has a temperature most suitable for responding to target DNA. Specifically, the result indicates that the nucleic-acid-responsive gel of the present invention shows the highest responsiveness to target DNA at 25° C., and that it is possible to control responsiveness to target DNA, i.e., detection accuracy, by changing a measurement temperature.

The present invention is not limited to the description of the embodiment above, but may be altered by a skilled person within the scope of the claims. An embodiment based on a proper combination of technical means disclosed in different embodiments is encompassed in the technical scope of the present invention.

INDUSTRIAL APPLICABILITY

As described above, in the nucleic-acid-responsive gel of the present invention, a probe formed of two single-stranded nucleic acids hybridized with each other is fixed inside the network structure of a polymer gel. In the probe, the two single-stranded nucleic acids are reversely bound with each other. With the arrangement, it is possible to recognize one base mismatch between nucleic acids from a volumetric change of the gel. It is accordingly expected that the nucleic-acid-responsive gel will be used as a material which makes it possible to identify a SNP, without requiring a special apparatus or a reagent as is required in a conventional technique. As compared to a conventional nucleic-acid-responsive gel containing one single-stranded nucleic acid as a probe, the nucleic-acid-responsive gel of the present invention is remarkably advantageous in that its recognition ability and response behavior can be freely controlled by adjusting the degree of base mismatches in a part where two single-stranded nucleic acids are hybridized with each other.

It is also expected that the nucleic-acid-responsive gel of the present invention will make it possible to provide a technique which is easy to handle because, by a synergetic effect of the network structure of a polymer gel, the nucleic-acid-responsive gel can convert a subtle difference at the molecular level between nucleic acids into macro information such as a volumetric change. With the diffusion of the nucleic-acid-responsive gel of the present invention as a genetic diagnosis material for various genes, it is expected that a totally new genetic diagnosis system etc. will be developed. This will make a remarkably large ripple effect in the field of tailor-made medical care etc. The nucleic-acid-responsive gel of the present invention can change its network structure in response to a target nucleic acid. This makes it possible to provide a totally new application system such as a nucleic-acid-responsive drug-release system. In conclusion, the present invention is applicable to and remarkably useful in various chemical industries such as pharmaceutical manufacturing industry, industrial chemical manufacturing industry, and further in medical industry.

The invention claimed is:

1. A nucleic-acid-responsive gel comprising a probe fixed inside a network structure of a polymer gel, wherein the probe comprises 0.1% or more of the dry weight of the gel, and wherein the probe comprises a first single strand of DNA, RNA, or PNA and a second single strand of DNA, RNA, or PNA,
wherein the first and the second single strand are substantially complementary to each other;
wherein the first or the second single strand is capable of hybridizing with a target nucleic acid;
wherein the probe forms a cross-linkage in a manner such that each of the first and second single strands of DNA, RNA, or PNA binds at a single point with a polymer compound constituting the network structure of the polymer gel, the single point being the only point where each of the first and second single strands is bound to the polymer compound;
wherein the nucleic-acid-responsive gel swells in response to the target nucleic acid; and wherein the nucleic-acid-responsive gel has a swelling ratio of 1.1 or higher, the swelling ratio being a value obtained by dividing a volume of the gel after a volumetric change after the gel swells by a volume of the gel before the volumetric change.

2. The nucleic-acid-responsive gel as set forth in claim 1, wherein the first and second single strands of DNA, RNA, or PNA have one or more base mismatches relative to each other when the first and the second single strands of DNA, RNA, or PNA are hybridized with each other.

3. The nucleic-acid-responsive gel as set forth in claim 1, wherein:
each of the first and the second single strands of DNA, RNA, or PNA has a 5' terminal bound with the polymer compound constituting the network structure of the polymer gel.

4. The nucleic-acid-responsive gel as set forth in claim 1, wherein:
each of the first and the second single strands of DNA, RNA, or PNA has a 3' terminal bound with the polymer compound constituting the network structure of the polymer gel.

5. The nucleic-acid-responsive gel as set forth in claim 1, wherein:
the first and the second single strands are both DNA, both RNA, or both PNA.

6. The nucleic-acid-responsive gel as set forth in claim 1, wherein: the polymer gel is:
obtained by polymerizing a monomer including at least one monomer selected from the group consisting of (meth)acrylamide, (meth)acrylic acid, 2-hydroxyethyl (meth)acrylate, alkyl (meth)acrylate, N,N'-dimethyl (meth)acrylamide, N-isopropyl (meth)acrylamide, vinyl acetate, and alkylamine; or
obtained by reacting the polymer compound selected from the group consisting of poly (meth) acrylamide, poly (meth) acrylic acid, poly-2-hydroxyethyl methacrylate, polyalkyl (meth)acrylate, poly-N,N'dimethyl (meth) acrylamide, poly-N-isopropyl (meth)acrylamide, polyvinyl alcohol, polyalkylamine, cellulose, chitosan, alginic acid, and derivatives thereof with a cross-linking agent so that the polymer gel has the network structure.

7. The nucleic-acid-responsive gel as set forth in claim 1, wherein:
the number of bases of the first and the second single strands of DNA, RNA, or PNA is 2 or more, but 10,000 or less.

8. The nucleic-acid-responsive gel as set forth in claim 1, wherein: the nucleic-acid-responsive gel decreases in cross-link density in response to the target nucleic acid that forms a more stable double strand in combination with any one of the first and second single strands of DNA, RNA, or PNA compared to a double strand formed by each of the first and second single strands of DNA, RNA, or PNA hybridized with each other.

9. The nucleic-acid-responsive gel as set forth in claim 1, wherein the nucleic-acid responsive gel is obtained by copolymerizing the probe with a monomer in presence or absence of a cross-linking agent, and further wherein each of the first and the second single strands of DNA, RNA, or PNA has a reactive functional group, and further wherein the monomer includes at least one monomer selected from the group consisting of (meth)acrylamide, (meth)acrylic acid, 2-hydroxyethyl (meth)acrylate, alkyl (meth)acrylate, N,N'-dimethyl (meth)acrylamide, N-isopropyl (meth)acrylamide, vinyl acetate, and allylamine.

10. The nucleic-acid-responsive gel as set forth in claim 1, wherein the nucleic-acid-responsive gel is obtained by a process comprising:
  (a) binding the probe to the polymer compound, wherein the probe is formed by the first and the second single strands of DNA, RNA, or PNA hybridized with each other, and wherein each of the first and the second single strands has a reactive functional group; and
  (b) reacting a mixture comprising the probe and the polymer compound obtained in the step (a) with a cross-linking agent, thereby forming the network structure of the polymer gel, the polymer compound being at least one selected from the group consisting of poly(meth)acrylamide, poly(meth)acrylic acid, poly-2-hydroxyethyl methacrylate, polyalkyl (meth)acrylate, poly-N,N'-dimethyl (meth)acrylamide, poly-N-isopropyl (meth)acrylamide, polyvinyl alcohol, polyalkylamine, cellulose, chitosan, alginic acid, and derivatives thereof.

11. A nucleic acid detection kit comprising the nucleic-acid-responsive gel recited in claim 1.

12. A nucleic acid detection apparatus comprising the nucleic-acid-responsive gel recited in claim 1.

* * * * *